(12) United States Patent
Surkov

(10) Patent No.: US 11,771,812 B2
(45) Date of Patent: *Oct. 3, 2023

(54) METHOD AND DEVICE FOR PURIFICATION OF BLOOD FROM CIRCULATING CELL FREE DNA

(71) Applicant: SANTERSUS AG, Zürich (CH)

(72) Inventor: Kirill Surkov, St. Petersburg (RU)

(73) Assignee: SANTERSUS AG, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/121,975

(22) Filed: Mar. 15, 2023

(65) Prior Publication Data

US 2023/0218810 A1    Jul. 13, 2023

Related U.S. Application Data

(63) Continuation of application No. 16/648,045, filed as application No. PCT/EP2018/075014 on Sep. 17, 2018, now Pat. No. 11,724,015.

(60) Provisional application No. 62/559,822, filed on Sep. 18, 2017.

(51) Int. Cl.
*A61M 1/34* (2006.01)

(52) U.S. Cl.
CPC ........ *A61M 1/3496* (2013.01); *A61M 1/3486* (2014.02); *A61M 2202/0415* (2013.01)

(58) Field of Classification Search
None
See application file for complete search history.

(56) References Cited

U.S. PATENT DOCUMENTS

| | | | |
|---|---|---|---|
| 4,824,432 A | 4/1989 | Skurkovich et al. | |
| 6,080,404 A | 6/2000 | Branham | |
| 6,528,057 B1 | 3/2003 | Ambrus et al. | |
| 6,774,102 B1 | 8/2004 | Bell et al. | |
| 7,612,032 B2 | 11/2009 | Genkin et al. | |
| 8,388,951 B2 | 3/2013 | Genkin et al. | |
| 8,431,123 B2 | 4/2013 | Genkin et al. | |
| 8,535,663 B2 | 9/2013 | Genkin et al. | |
| 8,916,151 B2 | 12/2014 | Genkin et al. | |
| 9,128,086 B2 | 9/2015 | Bawden et al. | |
| 9,248,166 B2 | 2/2016 | Genkin et al. | |
| 9,364,601 B2 | 6/2016 | Ichim et al. | |
| 9,402,944 B2 | 8/2016 | Selden et al. | |
| 9,642,822 B2 | 5/2017 | Wagner et al. | |
| 10,746,746 B2 * | 8/2020 | Eccleston | C12Q 1/6886 |
| 2007/0092509 A1 | 4/2007 | Mittra et al. | |
| 2008/0004561 A1 | 1/2008 | Genkin et al. | |
| 2009/0117099 A1 | 5/2009 | Esmon et al. | |
| 2011/0125286 A1 | 5/2011 | Selden et al. | |
| 2012/0226258 A1 | 9/2012 | Otto et al. | |
| 2012/0301487 A1 | 11/2012 | Mittra et al. | |
| 2013/0320858 A1 | 9/2013 | Cantor | |
| 2014/0099293 A1 | 4/2014 | Mittra et al. | |
| 2017/0035955 A1 | 2/2017 | Eliaz | |
| 2018/0024141 A1 | 1/2018 | Micallef et al. | |
| 2020/0261639 A1 | 8/2020 | Surkov | |

FOREIGN PATENT DOCUMENTS

| | | |
|---|---|---|
| CN | 105319374 A | 2/2016 |
| EP | 1666055 A1 | 6/2006 |
| EP | 2390662 A1 | 11/2011 |
| JP | 2004350502 | 12/2004 |
| RU | 2441674 C1 | 10/2012 |
| TW | 201819922 | 6/2018 |
| WO | 2005025650 A1 | 3/2005 |
| WO | 2007049286 | 3/2007 |
| WO | 2008047364 A2 | 4/2008 |
| WO | 2013084002 | 6/2013 |
| WO | 2014020564 A1 | 2/2014 |
| WO | 2017049279 | 3/2017 |
| WO | 2017068371 | 4/2017 |
| WO | 2017137495 | 8/2017 |
| WO | 2018119422 | 6/2018 |
| WO | 2019053243 | 3/2019 |
| WO | 2021038010 | 3/2021 |
| WO | 2021064463 | 4/2021 |

OTHER PUBLICATIONS

First Office Action issued in Application No. CN 201880067725.9 dated Feb. 27, 2023; with English Translation; 6 pages.
International Search Report and Written Opinion dated Apr. 18, 2023 in connection with PCT/IB2022/000665.
Atamaniuk, J. et al.,"Apoptotic Cell-Free DNA Promotes Inflammation in Haemodialysis Patients" Nephrol Dial Transplant (2012) vol. 27, pp. 902-905.
Brockers, K. et al., "Histone H1, the Forgotten Histone" Epigenomics (2019) vol. 11, No. 4, pp. 363-366.
Cao, H. et al., "Circulatory Mitochondrial DNA is a Pro-Inflammatory Agent in Maintenance Hemodialysis Patients" PLOS One (2014) vol. 9, No. 12, 14 pages total.
Czamanski-Cohen, J. et al., "Increased Plasma Cell-Free DNA is Associated with Low Pregnancy Rates Among Women Undergoing IVF-Embryo Transfer" Reproductive BioMedicine Online (2013) vol. 26, pp. 36-41.
Davis, JC et al., "Recombinant Human Dnase I (rhDNase) in Patients with Lupus Nephritis" Lupus (1999) vol. 8, pp. 68-76.
Gunjan, A. et al., "Effects of H1 Histone Variant Overexpression on Chromatin Structure" The Journal of Biological Chemistry (1999) vol. 274, No. 53, pp. 37950-37956.
Hergeth, S.P. et al., "The H1 Linker Histones: Multifunctional Proteins Beyond the Nucleosomal Core Particle" EMBO Reports (2015) vol. 16, No. 11, pp. 1439-1453.

(Continued)

*Primary Examiner* — Meera Natarajan
(74) *Attorney, Agent, or Firm* — Troutman Pepper Hamilton Sanders LLP

(57) ABSTRACT

The invention provides apheresis devices and their use for removal of substantially all types of cell free DNA (cfDNA) in patients' blood, including nucleosome-bound cfDNA, exosome-bound cfDNA and unbound cfDNA (including double stranded DNA (dsDNA), single stranded DNA (ssDNA) and oligonucleotides), to limit the negative effects of the circulating cfDNA and to treat various diseases.

3 Claims, 9 Drawing Sheets

Specification includes a Sequence Listing.

(56) References Cited

OTHER PUBLICATIONS

Kumar, P. et al., "Normal and Cancerous Tissues Release Extrachromosomal Circular DNA (eccDNA) into the Circulation" Mol Cancer Res (2017) vol. 15, No. 9, pp. 1197-1205.

Kusaoi, M. et al., "Separation of Circulating MicroRNAs Using Apheresis in Patients with Systemic Lupus Erythematosus" Therapeutic Apheresis and Dialysis (2016) vol. 20, No. 4, pp. 358-353.

Lintern, K.B. et al., "Immobilisation of Lactate Oxidase and Deoxyribonuclease I for Use Within a Bio-Artificial Liver Assist Device for the Treatment of Acute Liver Failure" University College London (2013) 209 pages total.

Simakova, E.S. et al., "An Experimental Support of the Use of Immobilized Decoxyribonuclease of Type I in the Treatment of Systemic Lupus Erythematosus" Abstract of Medical Science PhD Thesis (2011) 53 pages total.

Smith, B.J. et al., "Structural Homology Between a Mammalian H1 Subfraction and Avian Erythrocyte-Specific Histone H5" FEBS Letters (1980) vol. 112, No. 1, pp. 42-44.

Su, K-Y et al., "Mutational Monitoring of EGFR T790M in cfDNA for Clinical Outcome Prediction in EGFR-Mutant Lung Adenocarcinoma" PLOS One (2018) vol. 13, No. 11, 15 pages total.

"Terman, D.S. et al.," "Degardation of DNA and DNA: Anti-DNA Complexes by Extracorporeal Circulation over Nuclease Immobolized on Nylon Microspheres" "Abstract: The American Society of Nephrology (1975) 2 pages total."

Terman, S.D. et al., "'Degradation of Circulating DNA by Extracorporeal Circulation over Nuclease Immobilized on Nylon Microcapsules'" The Journal of Clinical Investigation (1976) vol. 57, pp. 1201-1212.

Terrell, J. et al., "Enrichment of Circulating Tumor DNA from Cell-Free DNA of Hematopoietic Origin" Journal of Clinical Oncology (2020) vol. 38, Issue 15, supplement, 3 pages total.

Trofimenko, A.S. et al., "Extracorporal Correction of Deteriorations of Catabolism of Nucleoproteins in a Model of Systemic Lupus Erythematosus. Efficiency and Safety Assessment in the Acute Experiment" Biomedical Chemistry (2015) vol. 61, pp. 622-627.

Tullis, R.H. et al., "Affinity Hemodialysis for Antiviral Therapy with Specific Application to HIV" Journal of Theoretical Medicine (2002) vol. 4, No. 3, pp. 157-166.

Yasuda, T. et al., "Abrupt Pubertal Elevation of Dnase I Gene Expression in Human Pituary Gland of Both Sexes" FEBS Letters (2002) vol. 510, pp. 22-26.

Zachariah, R. et al., "Circulating Cell-Free DNA as a Potential Biomarker for Minimal and Mild Endometriosis" Reproductive Biomedicine Online (2009) vol. 18, No. 3, pp. 407-411.

Communication (International Search Report) issued by the International Searching Authority in International Application No. PCT/EP2018/075014 dated Jan. 9, 2019, 4 pages total.

Communication (International Preliminary Report on Patentability) issued by the International Searching Authority in International Application No. PCT/EP2018/075014 dated Mar. 24, 2020, 7 pages total.

Communication (Written Opinion) issued by the International Searching Authority in International Application No. PCT/EP2018/075014 dated Jan. 9, 2019, 6 pages total.

Fukama, T., "Gene Therapy and Regulation" Gene Therapy and Regulation (2000) 2 pages total.

Wang, Z. et al., "Water-Soluble Adsorbent [beta]-cyclodextrin-grafted Polyethyleneimine for Removing Bilirubin from Plasma" Transfusion and Apheresis Science (2012) vol. 47, No. 2, pp. 159-165.

Communication (pursuant to Article 94(3) EPC) issued by the European Patent Office in European Application No. 18773736.6 dated Mar. 9, 2021, 4 pages total.

Office Action dated Sep. 13, 2021 in connection with Japanese Patent Application No. 2020-537046.

Office Action dated Dec. 2, 2021 in connection with Russian Application No. 2020113528.

G. Tokareva Issledovanye fetalnoy i materinskoy vnekletochnoy DNK pri normalnoy beremennosti i narusheniyakh razvitiay ploda. Abstract of the thesis. Tomsk, 2006, p. 19.

European Search Report dated Feb. 15, 2022 in connection with EP Application No. 21209617.

Atkinson A. et al., "Precipitation of nucleic acids with polyethyleneimine and the chromatography of nucleic acids and proteins on immobilised polyethyleeneimine", Biochimica Et Biophysica ACTA, Amsterdam, NL, vol. 308, No. 1, Apr. 21, 1973, pp. 41-52.

Lee J. et al., "Nucleic acid-binding polypers as anti-inflammatory agents", Proceedings of the National Academy of Sciences, vol. 108, No. 34, Aug. 23, 2011, pp. 14055-14060.

Office Action dated Mar. 15, 2022 in connection with Russian Application No. 2020113528.

Marleau A.M. et al., "Exosome removal as a therapeutic adjuvant in cancer", Journal of Translational Medicine, 2012, 10: 134, pp. 1-12.

International Search Report and Written Opinion dated Jan. 19, 2021 in connection with International Application No. PCT/IB2020/000817.

Lau P. P. et al., "A Rapid Method for the Purification of Supercoiled PM2 DNA by Affinity Chromatography on H1 Histone Covalently Coupled to Agarose", Biochimica et Biophysica Acta, 563 (1979) pp. 313-319.

Yu S. et al., "Chromatography of Different Forms of DNA on Immobilized Histone Columns", Biochimica et Biophysica Acta, 517 (1978) pp. 31-42.

International Preliminary Report on Patentability dated Apr. 5, 2022 in connection with PCT Application No. PCT/IB2020/000817.

European Search Report dated May 10, 2022 in connection with EP Application No. 21209611.9.

Licht et al., "Plasma levels of nucleosomes and nucleosome-autoantibody complexes in murine lupus: Effects of disease progression and lipopolysaccharide administration", Athritis and Rheumatism, vol. 44, No. 6, Jun. 1, 2001, pp. 1320-1330.

Bauden et al., "Cirulating nucleosome as epigenic biomarkers in pancreatic cancer", Clinical Epigentics, Biomed Central Ltd., London, UK, vol. 7, No. 1, Oct. 7, 2015, p. 106.

Restriction Requirement dated Sep. 8, 2022 in connection with U.S. Appl. No. 16/648,045.

International Search Report and Written Opinion dated Sep. 19, 2022 in connection with PCT/IB2022/000192.

Thalin Charlotte et al., "Quantification of citrullinated histones: Development of an improved assay to reliability quantify nucleosomal H3Cit in human plasma" Journal of Thrombosis and Haemostasis, vol. 18, No. 10, Aug. 8, 2020, pp. 2732-2743.

Tsourouktsoglou Theodora-Dorita et al., "Histones, DNA, and Citrullination Promote Neutrophil Extracellular Trap Inflammation by Regulating the Localization and Activation of TLR4", Cell Reports, vol. 31, No. 5, May 1, 2020, pp. 107602.

Office Action dated Nov. 21, 2022 in connection with U.S. Appl. No. 16/648,045.

Tanaka et al., "Expression and purification of recombinant human histones" Methods, 2004, 33(1):3-11.

Dyer et al., "Reconstitution of Nucleosome Core Particles from Recombinant Histones and DNA" Methods Enzymol., 2003, 375:23-44.

Ross et al., "Optimization of ligand presentation for immunoadsorption using star-configured polythylene glycols" J Biomed Mater Res, 2000, 51:29-36.

* cited by examiner

SEQUENCE LISTING

```
Sequence total quantity: 3
SEQ ID NO: 1            moltype = DNA  length = 19
FEATURE                 Location/Qualifiers
source                  1..19
                        mol_type = other DNA
                        organism = synthetic construct
SEQUENCE: 1
tcctacggga ggcagcagt                                                        19

SEQ ID NO: 2            moltype = DNA  length = 26
FEATURE                 Location/Qualifiers
source                  1..26
                        mol_type = other DNA
                        organism = synthetic construct
SEQUENCE: 2
ggactaccag ggtatctaat cctgtt                                                26

SEQ ID NO: 3            moltype = DNA  length = 23
FEATURE                 Location/Qualifiers
source                  1..23
                        mol_type = other DNA
                        organism = synthetic construct
modified_base           1
                        mod_base = OTHER
                        note = 6-Carboxyfluorescein modified nucleotide
modified_base           23
                        mod_base = OTHER
                        note = Tetramethylrhodamine (TAMRA) azide modified
                         nucleotide
SEQUENCE: 3
cgtattaccg cggctgctgg cac                                                   23
```

METHOD AND DEVICE FOR PURIFICATION OF BLOOD FROM CIRCULATING CELL FREE DNA

CROSS-REFERENCE TO RELATED APPLICATIONS

This application is a continuation of U.S. application Ser. No. 16/648,045, filed Mar. 17, 2020, which is a National Stage of PCT/EP2018/075014, filed on Sep. 17, 2018, which claims priority to U.S. Provisional Patent Application No. 62/559,822, filed on Sep. 18, 2017, all of which are incorporated herein by reference in their entirety.

SEQUENCE LISTING

The instant application contains a Sequence Listing which has been submitted electronically in XML format and is hereby incorporated by reference in its entirety. Said XML copy, created on May 22, 2023, is named 252176_000051_SL.xml and is 4,842 bytes in size.

FIELD OF THE INVENTION

The invention provides apheresis devices and their use for removal of substantially all types of cell free DNA (cfDNA) in patients' blood, including nucleosome-bound cfDNA, exosome-bound cfDNA and unbound cfDNA (including double stranded DNA (dsDNA), single stranded DNA (ssDNA) and oligonucleotides), to limit the negative effects of the circulating cfDNA and to treat various diseases.

BACKGROUND OF THE INVENTION

Circulating extracellular DNA (eDNA), also called cell free DNA (cfDNA), is present in small amounts in the blood of healthy individuals.

Increased levels of circulating cfDNA is now a widely accepted as marker for a number of diseases and pathological conditions including but not limited to cancer, metastatic cancer, acute organ failure, organ infarct (including myocardial infarction and ischemic stroke), hemorrhagic stroke, autoimmune disorders, graft-versus-host-disease (GVHD), graft rejection, sepsis, systemic inflammatory response syndrome (SIRS), multiple organ dysfunction syndrome (MODS), graft-versus-host-disease (GVHD), traumatic injury, proinflammatory status in aged individuals, diabetes, atherosclerosis, neurodegenerative disease, autoimmune disease, eclampsia, infertility, coagulation disorder, pregnancy-associated complications and infection. Different subtypes of circulating cell free DNA might play a significant role in progression of certain diseases and pathological conditions.

It was proposed to use systemic administration of Deoxyribonuclease (DNase) enzyme, which specifically hydrolyzed circulating cfDNA for treatment of infertility (U.S. Pat. No. 8,916,151); cardiovascular disorders (U.S. Pat. No. 9,642,822); cancer; sepsis, graft-versus-host-disease (GBHD); organ failure; diabetes; atherosclerosis; delayed-type hypersensitivity reactions (U.S. Pat. Nos. 9,248,166; 8,535,663; 7,612,032; 8,388,951; 8,431,123).

However, contrary to early stage animal models, data in real clinical settings has shown that systemic application of deoxyribonuclease (DNase) enzyme has limited effects on reducing the quantity of circulating cfDNA.

Hazout, A. (PCT/IB2013/056321) has described 10 women with high levels of circulating cfDNA (>80 ng/µl) treated with 0.1 mg/kg of DNaseI daily via intramuscular route twice a day for seven days and observed only an average 26% decrease in the level of circulating cfDNA. Their observations were in line with Davis et al., who failed to demonstrate the reduction of circulating level of alpha DS DNA in lupus nephritis patients receiving a 25 µg/kg dose of human recombinant deoxyribonuclease as a total of one intravenous and ten subcutaneous injections over a period of 19 days despite achievement in plasma of catalytically effective deoxyribonuclease concentrations between 40-100 ng/ml. (Davis J. C. et al., Recombinant human Dnase I (rhDNase) in patients with lupus nephritis Lupus (1999) Vol 8 (1), pp. 68-76.)

The most abundant type of circulating cfDNA is represented by nucleosome-bound DNA. A nucleosome is a subunit of nuclear chromatin and consists of a central core protein formed by an octamer of the double-represented core histones and about 147 base pairs of double-stranded DNA (Oudet P, Gross-Bellard M, Chambon P. Electron microscopic and biochemical evidence that chromatin structure is a repeating unit. Cell. 1975; 4:281-300). Nucleosome-bound cfDNA might circulate in blood as mononucleosomes or higher order structures such as oligonucleosomes or even fragments of chromatin containing over $50\text{-}100\times10^3$ base pairs of DNA. This particular type of circulating cfDNA originates from cells undergoing necrosis or apoptosis. Another source circulating cfDNA is neutrophil NETosis. Neutrophil extracellular traps (NETs), which are extracellular strands of decondensed DNA expelled from activated neutrophils, have over $15\times10^3$ base pairs of DNA length that are organized in 3D net structures of 10-30 nm. NETosis originating cfDNA might be either particle free or particle bound. NETs olso contain highly cytotoxic enzymes and cytrotoxic proteins originating from neutrophil interior space. (Srensen, O. E. and Borregaard, N., Neutrophil extracellular traps—the dark side of neutrophils. J. Clin. Invest. 2016 May 2; 126(5): 1612-20.) It has been shown recently that not only neutrophils but also macrophages might produce NET like structures (Nat Med., 2018, 24(2):232-238).

Another important type of circulating particle bound cfDNA is exosome-bound DNA. Exosomes are small membrane vesicles (30-100 nm) of exocytotic origin secreted by most cell types that might contain single-stranded DNA (ssDNA), mitochondrial DNA (mtDNA) and double-stranded (dsDNA) of $2.5\text{-}10\times10^3$ base pairs at the inner or outer space of exosome. (Thakur, B. K. et al., Double-stranded DNA in exosomes: a novel biomarker in cancer detection, Cell Research (2014) 24:766-769.)

A significant part of circulating cfDNA free of particles is represented by linear and circular dsDNA and ssDNA secreted by cancer cells, activated immune cells and certain other cell types. This type of cfDNA is generally 250-1000 base pairs length or higher and may be enriched in unique genome sequences. (Kumar, P. et al., Normal and cancerous tissues release extrachromosomal circular DNA (eccDNA) into the circulation, Mol. Cancer. Res., Jun. 20, 2017 DOI: 10.1158/1541-7786.MCR-17-0095.) Another important constituent of circulating cfDNA free of particles is mitochondrial DNA (mtDNA) of different lengths.

Another recently discovered type of particle-free circulating cfDNA is represented by ultra short double stranded DNA (dsDNA) oligonucleotides and single stranded DNA (ssDNA) oligonucleotides with a subnucleosomal length (i.e. usually less than ~147 base pairs). It was shown that this particular cfDNA is enriched in mitochondrial DNA (mtDNA), DNA of microbial origin and mutated human genome sequences. (Burnham P., Single-stranded DNA library preparation uncovers the origin and diversity of ultrashort cell-free DNA in plasma, Scientific Reports 6, Article number: 27859 (2016), doi:10.1038/srep27859). Importantly, this type of circulating cfDNA also contains the low molecular weight DNA fragments which are similar of those that appear following degradation of particle bound DNA by DNase I enzyme in blood of patients.

Several attempts have been made to use extracorporeal removal technologies to purify patient blood from certain constituents of circulating cfDNA pool. See, e.g., U.S. Pat. No. 9,364,601; U.S. Patent Application Publication No. 2007/0092509; Kusaoi et al., Ther. Apher. Dial, 2016, 20:348-353.

There is a need for new extracorporeal methods of treating diseases associated with high circulating level of blood cfDNA and for new more effective devices to realize such methods.

SUMMARY OF THE INVENTION

As specified in the Background section, above, there is a need for new extracorporeal methods of treating diseases associated with high level of circulating blood cfDNA and for new more effective devices to realize such methods. The present invention addresses this and other needs by providing apheresis devices and associated processes.

In one aspect, the invention provides a device configured to perform apheresis comprising one or more affinity matrices, wherein said one or more affinity matrices are capable of capturing nucleosome-bound cell free DNA (cfDNA), exosome-bound cfDNA, and unbound cfDNA from blood or plasma of a subject.

In some embodiments, the unbound cfDNA comprises dsDNA, ssDNA and oligonucleotides.

In some embodiments, the device of the invention comprises two or more affinity matrices. In some embodiments (i) the first one or more affinity matrices is capable of capturing nucleosome-bound cell free DNA (cfDNA) and/or exosome-bound cfDNA and (ii) the second one or more affinity matrices is capable of capturing unbound cfDNA, and wherein the first and second affinity matrices are arranged within the device in any order. In some embodiments, (i) the first one or more affinity matrices comprises a DNA binding protein (e.g., a histone [e.g., a H1 histone]), an anti-histone antibody (e.g., an anti-histone H2A antibody), an anti-nucleosome antibody (e.g., AN-1, AN-44), a DNA intercalating agent (e.g., a Hoechst dye such as, e.g., Hoechst 33342), a DNA-binding polymer (e.g., a cationic/basic polymer [e.g., polyethylenimine, poly-L-lysine, poly-L-arginine, hexadimethrine bromide, amino terminated (—NH$_2$) polyamidoamine (PAMAM) dendrimer, polypropyleneimine (PPI) dendrimer], a non-ionic/neutral polymer [e.g., polyvinylpyrrolidone (PVP), polyvinylpolypyrrolidone (PVPP), poly (4-vinylpyridine-N-oxide)], an anionic/acidic polymer; a linear polymer [e.g., polyethylenimine, poly-L-lysine, poly-L-arginine], a branched polymer [e.g., hyper-branched poly-L-lysine, hyper-branched polyethylenimine], a dendrimeric polymer [e.g., polyamidoamine (PAMAM) dendrimer, polypropyleneimine (PPI) dendrimer]), an anti-DNA antibody (e.g., mouse monoclonal IgM Anti-ds+ss DNA antibody ([49/4A1], ab35576, Abcam), a lectin (e.g., *Galanthus nivalis* Lectin (GNA), *Narcissus Pseudonarcissus* Lectin (NPA), Conconavalin A, phytohemagluttanin, or cyanovirin), and any combination thereof, and (ii) the second one or more affinity matrices comprises a DNA binding protein (e.g., a histone [e.g., a H1 histone]), a DNA intercalating agent (e.g., a Hoechst dye such as, e.g., Hoechst 33342), a DNA binding polymer (e.g., a cationic/basic polymer [e.g., polyethylenimine, poly-L-lysine, poly-L-arginine, hexadimethrine bromide, polyamidoamine (PAMAM) amino terminated (—NH$_2$) dendrimer, polypropyleneimine (PPI) dendrimer], a non-ionic/neutral polymer [e.g., polyvinylpyrrolidone (PVP), polyvinylpolypyrrolidone (PVPP), poly (4-vinylpyridine-N-oxide)], anionic/acidic polymers; linear polymers [e.g., polyethylenimine, poly-L-lysine, poly-L-arginine], a branched polymer [e.g., hyper-branched poly-L-lysine, hyper-branched polyethylenimine], a dendrimeric polymer [e.g., polyamidoamine (PAMAM) dendrimer, polypropyleneimine (PPI) dendrimer]), an anti-DNA antibody (e.g., mouse monoclonal IgM Anti-ds+ss DNA antibody ([49/4A1], ab35576, Abcam), and any combination thereof. In some embodiments, said two or more affinity matrices are sequentially arranged as two or more affinity columns. In some embodiments, the first affinity matrix in the sequence comprises a DNA binding polymer (e.g., amino terminated (—NH$_2$) polyamidoamine (PAMAM) dendrimer, polypropyleneimine (PPI) dendrimer, hyper-branched poly-L-lysine, or hyper-branched polyethylenimine) or a DNA intercalating agent (e.g., Hoechst 33342). In certain embodiments, the affinity matrix is not polyamidoamine (PAMAM) dendrimer.

Non-limiting examples of useful column combinations (arranged in any order) are as follows: (a)(i) DNA intercalating agent Hoechst 33342 affinity column and (ii) anti-DNA antibody affinity column; or (b) (i) anti-nucleosome antibody affinity matrix (ANAM) column and (ii) anti-DNA antibody affinity column; or (c) (i) anti-nucleosome antibody affinity matrix (ANAM) column and (ii) polyamidoamine dendrimer affinity matrix (PDAM) column; or (d) (i) anti-nucleosome antibody affinity matrix (ANAM) column and (ii) hyper-branched poly-L-lysine affinity matrix (PLLAM) column; or (e) (i) anti-histone H2A antibody affinity column, (ii) lectin affinity column, and (iii) histone H1 affinity column or polyamidoamine dendrimer affinity matrix (PDAM) column or hyper-branched poly-L-lysine affinity matrix (PLLAM) column or DNA intercalating agent Hoechst 33342 affinity column.

In some embodiments, the device of the invention comprises a single affinity matrix. Non-limiting examples of useful matrices which can be used as a single affinity matrix include: affinity matrices comprising a histone (e.g., histone H1 such as, e.g., histone H1.3), affinity matrices comprising a DNA binding polymer (e.g., a cationic polymer such as, e.g., amino terminated (—NH$_2$) polyamidoamine (PAMAM) dendrimer or hyper-branched poly-L-lysine), affinity matrices comprising a DNA intercalating agent (e.g., Hoechst 33342), affinity matrices comprising an anti-DNA antibody (e.g., mouse monoclonal IgM Anti-ds+ss DNA antibody ([49/4A1], ab35576, Abcam). In certain embodiments, the affinity matrix is not polyamidoamine (PAMAM) dendrimer.

In some embodiments, the device of the invention captures at least 30 mg of cfDNA per single apheresis procedure.

In some embodiments, the device of the invention reduces the blood level of cfDNA by at least 25% per single apheresis procedure. In some embodiments, the device of the invention reduces the blood level of cfDNA by at least 50% per single apheresis procedure. In some embodiments, the device of the invention reduces the blood level of cfDNA by at least 75% per single apheresis procedure.

In another aspect, the invention provides a method of reducing the level of cell free DNA (cfDNA) in the blood of a subject, the method comprising: (a) performing an apheresis procedure comprising diverting blood or plasma from the subject into an apheresis device of the present invention to produce blood or plasma with reduced levels of the cfDNA; and (b) returning the blood or plasma with reduced levels of the cfDNA to the subject, wherein the apheresis procedure reduces the level of nucleosome-bound cfDNA, exosome-bound cfDNA, and unbound cfDNA in the blood of the subject. In some embodiments, the subject has a disease characterized by elevated level of cfDNA in the blood. In some embodiments, the subject has a disease selected from the group consisting of a neurodegenerative disease, a cancer, a chemotherapy-related toxicity, an irradiation induced toxicity (e.g., acute radiation syndrome), an organ failure, an organ injury, an organ infarct, ischemia, an acute vascular event, a stroke, graft-versus-host-disease (GVHD), graft rejection, sepsis, systemic inflammatory response syndrome (SIRS), multiple organ dysfunction syndrome (MODS), a traumatic injury, aging, diabetes, atherosclerosis, an autoimmune disorder, eclampsia, infertility, a pregnancy-associated complication, a coagulation disorder, and an infection.

In a further aspect, the invention provides a method of treating a disease in a subject in need thereof, the method comprising: (a) performing an apheresis procedure comprising diverting blood or plasma from the subject into an apheresis device of the present invention to produce the blood or plasma with reduced levels of the cfDNA; and (b) returning the blood or plasma with reduced levels of the cfDNA to the subject, wherein the apheresis procedure reduces the level of nucleosome-bound cfDNA, exosome-bound cfDNA, and unbound cfDNA in the blood of the subject. In some embodiments, the subject has a disease characterized by elevated level of cfDNA in the blood. Non-limiting examples of diseases treatable by the methods of the invention include, e.g., a neurodegenerative disease, a cancer, a chemotherapy-related toxicity, an irradiation induced toxicity (e.g., acute radiation syndrome), an organ failure, an organ injury, an organ infarct, ischemia, an acute vascular event, a stroke, graft-versus-host-disease (GVHD), graft rejection, sepsis, systemic inflammatory response syndrome (SIRS), multiple organ dysfunction syndrome (MODS), a traumatic injury, aging, diabetes, atherosclerosis, an autoimmune disorder, eclampsia, infertility, a pregnancy-associated complication, a coagulation disorder, and an infection.

In some embodiments of any of the above methods of the invention, the method further comprises monitoring the level of cfDNA in the blood of the subject.

In some embodiments of any of the above methods of the invention, the method comprises continuing or repeating the apheresis procedure until the level of cfDNA is reduced by at least 25%. In some embodiments of any of the above methods of the invention, the method comprises continuing or repeating the apheresis procedure until the level of cfDNA is reduced by at least 50%. In some embodiments of any of the above methods of the invention, the method comprises continuing or repeating the apheresis procedure until the level of cfDNA is reduced by at least 75%.

In some embodiments of any of the above methods of the invention, the method comprises continuing or repeating the apheresis procedure until at least 30 mg of cfDNA is removed from the blood of the subject.

In some embodiments of any of the above methods of the invention, the apheresis procedure is repeated two or more times.

In some embodiments of any of the above methods of the invention, the blood for the apheresis procedure is sourced from the portal vein.

In some embodiments of any of the above methods of the invention, the unbound cfDNA comprises dsDNA, ssDNA and oligonucleotides.

In some embodiments of any of the above methods of the invention, the subject is human.

These and other aspects of the present invention will be apparent to those of ordinary skill in the art in the following description, claims and drawings.

BRIEF DESCRIPTION OF THE DRAWINGS

FIG. 2A shows tumors excised from control group mice. FIG. 2B shows tumors excised from mice treated with DNA from an NSCLC T3N2M+ patient purified from nucleosome and exosome bound circulating cfDNA.

DETAILED DESCRIPTION OF THE INVENTION

Definitions

Figure 1:
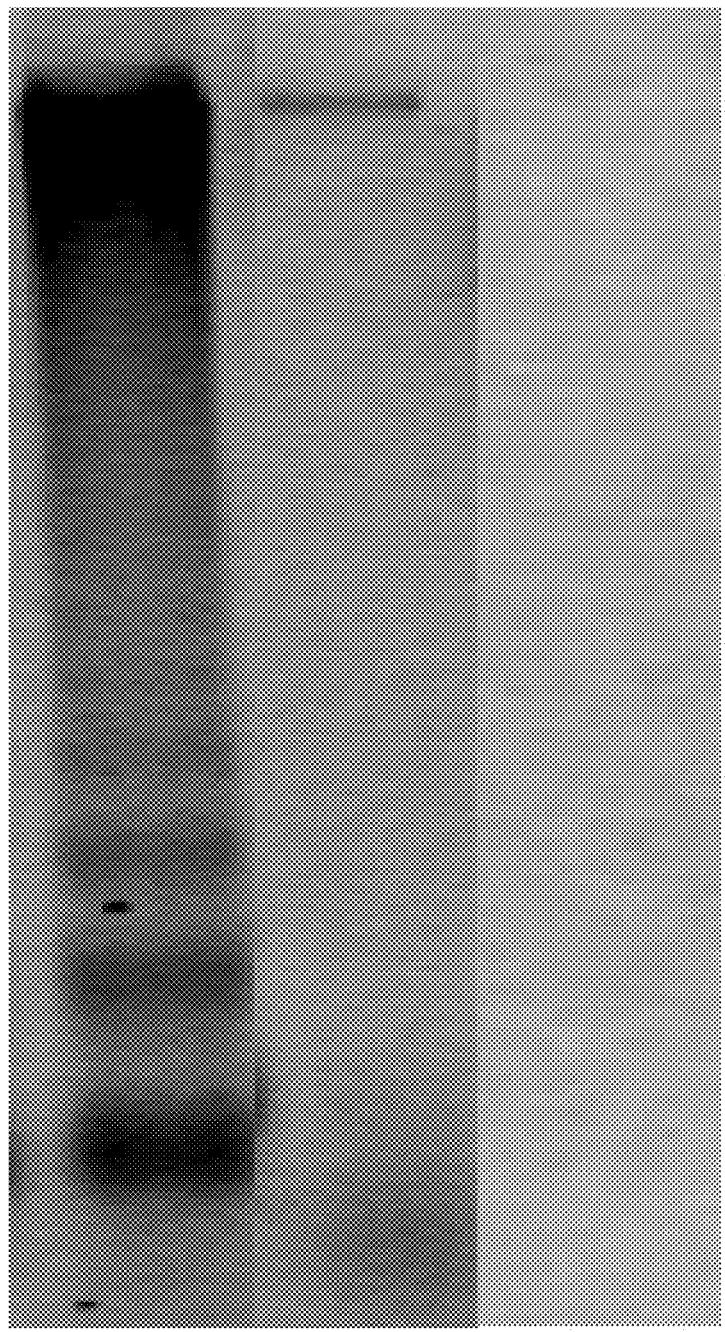
FIG. 1 shows an electrophoretic profile of circulating cfDNA from plasma of a metastatic cancer patient.

Unless defined otherwise, all technical and scientific terms used herein have the same meaning as commonly understood by one of ordinary skill in the art to which this invention belongs.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "device" as used herein refers to any assembly known in the art to enable the purification of liquid solutions, such as, without limitation, e.g., any hollow-ware, a column, a column matrix, a filter, a membrane, a semipermeable material, a bead (e.g., a microbead or a nanobead), or a tubing. The terms "column" and "cartridge" are used interchangeably herein in the context of an apheresis device.

The term "affinity matrix" as used herein refers to (i) a solid support into which a ligand (e.g., a cfDNA-binding molecule) is immobilized or to (ii) a solid support formed by the ligand itself (e.g., a water-insoluble DNA-binding polymer).

The term "DNA-binding protein" refers to proteins that bind to single-stranded DNA (ssDNA) or double-stranded DNA (dsDNA). DNA binding proteins can bind DNA in sequence-specific manner (e.g., transcription factors and nucleases) or non-sequence specifically (e.g., polymerases and histones). The linker histone H1 family members are a key component of chromatin and bind to the nucleosomal core particle around the DNA entry and exit sites.

As used herein, the terms "circulating DNA", "cell free DNA (cfDNA)", "circulating cell free DNA (cfDNA)", "extracellular DNA (eDNA)", and "circulating extracellular DNA (eDNA)" are used interchangeably to refer to DNA present in blood or plasma located outside of circulating cells of hematopoietic and non-hematopoietic origin.

Nucleosome-bound cfDNA is DNA that is bound to a nucleosome. A nucleosome is a subunit of nuclear chromatin. Nucleosome-bound cfDNA might circulate in blood as mononucleosomes or higher order structures such as oligonucleososmes or even fragments of chromatin containing over $50\text{-}100 \times 10^3$ base pairs of DNA. Circulating nucleosome-bound cfDNA may originate from cells undergoing necrosis or apoptosis and from neutrophil NETosis.

Exosome-bound cfDNA is cfDNA that is bound to exosomes or present in exosomes. Exosomes are small membrane vesicles (about 30-100 nm) of exocytotic origin secreted by most cell types that might contain single-stranded DNA (ssDNA), mitochondrial DNA (mtDNA) and double-stranded DNA (dsDNA) at the inner or outer space of exosome.

The terms "unbound cfDNA" or "cfDNA free of particles" or "particle free cfDNA" refer to cfDNA which is not bound to exosomes or nucleosomes and encompasses double-stranded DNA (dsDNA), single-stranded DNA (ssDNA), linear or circular and oligonucleotides, including ultrashort DNA molecules of subnucleosomal size (usually less than 147 base pairs).

As used herein, the terms "subject" and "patient" are used interchangeably and refer to animals, including mammals such as humans, veterinary animals (e.g., cats, dogs, cows, horses, sheep, pigs, etc.), and experimental animal models. In certain embodiments, the subject refers to a human patient, including both genders in adult and child populations.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof, or (3) relieving the disease, i.e., causing regression of the state, disorder or condition or at least one of its clinical or sub-clinical symptoms.

The practice of the present invention employs, unless otherwise indicated, conventional techniques of statistical analysis, molecular biology (including recombinant techniques), microbiology, cell biology, conjugation chemistry and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ. Hermanson (2013) Bioconjugate Techniques, 3rd ed., Academic Press; Niemeyer (2004) Bioconjugation Protocols: Strategies and Methods, Springer Science & Business Media and Hermanson et al. (1992) Immobilized Affinity Ligand Techniques, Academic Press. Additional techniques are explained, e.g., in U.S. Pat. No. 7,912,698 and U.S. Patent Appl. Pub. Nos. 2011/0202322 and 2011/0307437.

Devices and Methods of the Invention

As specified in the Background Section, there is a great need in the art to develop new methods and devices for reducing the level of substantially all types of circulating cfDNA in the blood. The present disclosure addresses this and other needs by providing apheresis devices and methods, wherein the apheresis device reduces the level of substantially all types of cfDNA, including nucleosome-bound cfDNA, exosome-bound cfDNA and unbound cfDNA (including dsDNA, ssDNA and oligonucleotides).

The use of extracorporeal removal technologies can provide an effective solution to eliminate cfDNA from circulation and, correspondingly, decrease the level and negative effects of circulating cfDNA. Therapeutic apheresis is an extracorporeal treatment that removes blood components from patients; it is used for the treatment of conditions in which a pathogenic substance or component in the blood is causing development of diseases: see for example, Ward M. D., Conventional Apheresis Therapies: A Review Journal of Clinical Apheresis 26:230-238 (2011).

Surprisingly, as demonstrated herein, extracorporeal removal of substantially all types of circulating cfDNA has a positive impact on the treatment of diseases characterized by elevated circulating levels of cfDNA in the blood.

The present disclosure provides a method for treating diseases characterized by elevated circulating levels of cfDNA through the removal of substantially all types of cfDNA, including nucleosome-bound cfDNA, exosome-bound cfDNA and unbound cfDNA (including dsDNA, ssDNA and oligonucleotides) from the blood of a subject to reduce the negative effects of the circulating cfDNA.

Without wishing to be bound by theory, in certain diseases, wherein the level of circulating cfDNA is increased, different types of circulating cfDNA might act in concert by triggering different molecular pathways each leading to disease progression and patient mortality; different types of circulating cfDNA acting together might generate synergistic toxicity, i.e.toxic (negative) effect of two or more types of circulating cfDNA is greater than the sum of the negative effects of each type of cfDNA taken separately.

The inventors have found that removal of substantially all types of cfDNA, including nucleosome-bound cfDNA, exosome-bound cfDNA and unbound cfDNA (including double stranded DNA [dsDNA], single stranded DNA [ssDNA] and oligonucleotides) from the blood of patients with increased levels of circulating cfDNA can effectively reduce or even fully abolish the pathogenic effects mediated by said circulating cfDNA. Removal of substantially all types of cfDNA, including nucleosome-bound cfDNA, exosome-bound cfDNA and unbound cfDNA (dsDNA, ssDNA and oligonucleotides) appears critical for reducing pathogenic effects mediated by cfDNA.

The inventors further surprisingly observed that removal of substantially all types of circulating cfDNA might lead to reactivation of endogenous deoxyribonucleases.

It is further described herein that several affinity matrices or combinations thereof are able to effectively capture substantially all types of cfDNA, including nucleosome-bound cfDNA, exosome-bound cfDNA and unbound cfDNA (including dsDNA, ssDNA and oligonucleotides) from the blood of patients in need thereof. Examples of affinity matrices useful in apheresis devices and methods of the invention include (i) matrices comprising a DNA binding protein (e.g., a histone [e.g., a H1 histone]), (ii) matrices comprising an anti-histone antibody (e.g., an anti-histone H2A antibody), an anti-nucleosome antibody (e.g., AN-1, AN-44), (iii) matrices comprising a DNA intercalating agent (e.g., a Hoechst dye such as, e.g., Hoechst 33342), (iv) matrices comprising a DNA-binding polymer (e.g., a cationic/basic polymer [e.g., polyethylenimine, poly-L-lysine, poly-L-arginine, hexadimethrine bromide, amino terminated (—NH$_2$) polyamidoamine (PAMAM) dendrimer, polypropyleneimine (PPI) dendrimer], a non-ionic/neutral polymer [e.g., polyvinylpyrrolidone (PVP), polyvinylpolypyrrolidone (PVPP), poly (4-vinylpyridine-N-oxide)], an anionic/acidic polymer; a linear polymer [e.g., polyethylenimine, poly-L-lysine, poly-L-arginine], a branched polymer [e.g., hyper-branched poly-L-lysine, hyper-branched polyethylenimine], a dendrimeric polymer [e.g., polyamidoamine (PAMAM) dendrimer, polypropyleneimine (PPI) dendrimer; see, e.g., Kaur et al., J Nanopart Res., 2016, 18:146]; see, e.g., U.S. Pat. No. 7,713,701 and Morozov et al., General Reanimatology, 2016, 12:6 for additional examples), (v) matrices comprising an anti-DNA antibody, (vi) matrices comprising a lectin (e.g., *Galanthus nivalis* Lectin (GNA), *Narcissus Pseudonarcissus* Lectin (NPA), Conconavalin A, phytohemagluttanin, or cyanovirin), and any combination thereof. In some embodiments, two or more affinity matrices are sequentially arranged as two or more affinity columns. In some embodiments, the first affinity matrix in the sequence comprises a DNA binding polymer (e.g., amino terminated (—NH$_2$) polyamidoamine (PAMAM) dendrimer, polypropyleneimine (PPI) dendrimer, hyper-branched poly-L-lysine, or hyper-branched polyethylenimine) or a DNA intercalating agent (e.g., Hoechst 33342).

Described herein are affinity matrices and apheresis devices comprising such matrices. An apheresis device of the invention may be configured according to the knowledge of one of ordinary skill in the art, for example as described in U.S. Patent Application No. 2017/0035955 (Eliaz Issac. published February 9,2017)). In one possible embodiment of the apheresis device, affinity matrices are placed into various affinity columns, or cartridges. The apheresis device can comprise a filtration cartridge and one or more affinity columns having an inlet and an outlet, in which the device is capable of capturing nucleosome-bound cfDNA, exosome-bound cfDNA and unbound cfDNA (including dsDNA, ssDNA and oligonucleotides), from blood or plasma of a patient. In some embodiments, the device comprises two or more affinity columns in sequence. The inlet and outlet can be positioned with respect to the affinity matrices such that blood entering the inlet must contact the affinity matrices before exiting through the outlet. Preferably, the geometry of the device is designed to maximize contact of blood (or plasma) with the affinity matrices during passage through the device. A variety of such designs are known in the art. For example, the device can be a hollow cylinder packed with an affinity ligand immobilized on beads, having the inlet at one end and the outlet at the opposite end. Other devices, such as microtubule arrays, can be also constructed. All such variations of container geometry and volume and of the affinity matrices contained therein can be designed according to known principles. In preparing an affinity matrix column, the affinity matrix may be loaded to at least 50%, 60%, 70%, 75%, 80%, 85%, or 90% column volume. A suitable buffer (e.g., PBS, particularly cold PBS) may be used to equilibrate the column.

In one aspect is provided a histone affinity matrix comprising cellulose beads and recombinant human histone H1.3, wherein the recombinant human histone H1.3 is immobilized on the cellulose beads and wherein the size of the beads is between 50 and 350 micrometers. In some embodiments, the size of the beads is between 100 and 250 micrometers.

In some embodiments, the histone affinity matrix is prepared by a process comprising
  a) oxidizing cellulose beads having a size between 100 and 250 micrometers to yield activated cellulose beads;
  b) washing the activated cellulose beads;
  c) preparing a concentrated solution of recombinant human histone H1.3;
  d) incubating the activated cellulose beads with the concentrated solution of recombinant human histone H1.3; and e) blocking any free CHO groups on the activated cellulose beads.

In some embodiments, the process further comprises f) washing the activated cellulose beads with buffer.

In some embodiments, in step a) the cellulose beads are in an aqueous suspension and oxidized with NaIO. In some embodiments, in step b), the activated cellulose beads are washed with sodium bicarbonate, hydrochloric acid and water. In some embodiments, step c) comprises dialyzing a solution of recombinant human histone H1.3 and concentrating the dialyzed solution in 0.1 M NaHCO$_3$ at pH 7-9. In some embodiments, the dialyzed solution is concentrated in 0.1 M NaHCO$_3$ at pH 8. In some embodiments, in step d) the incubation is performed for 3-5 hours at 15-30° C. In some embodiments, in step d) the incubation is performed for 4 hours at room temperature. In some embodiments, in step e) the blocking step comprises adding 1 M ethanolamine to the activated cellulose beads and reacting for 30 minutes to 2 hours at 15-30° C.

In some embodiments, in step f) the activated cellulose beads are washed with TBS buffer.

Also provided is a column comprising the histone affinity matrix of any of the aspects and embodiments above.

In another aspect is provided a lectin affinity matrix prepared according to a process comprising
 a) reacting lectin with activated agarose beads to yield lectin-coupled agarose; and
 b) washing the lectin-coupled agarose with buffer.

In some embodiments, the lectin is from *Galanthus nivalis* (snowdrop). In some embodiments, the activated agarose beads are CNBr activated agarose beads. In some embodiments, the buffer is PBS, such as sterile cold PBS at pH 7.2-7.4.

Also provided is a column comprising the lectin affinity matrix of any of the aspects and embodiments above.

In yet another aspect is provided a polyamidoamine dendrimer affinity matrix (PDAM) prepared by a process comprising
 a) washing cellulose beads with ethanol and water;
 b) incubating the washed cellulose beads with (±)-epichlorohydrin and NaOH to yield activated cellulose beads;
 c) reacting the activated cellulose beads with polyamidoamine (PAMAM) dendrimer to yield PDAM beads and removing PAMAM dendrimer that did not react with the activated cellulose beads; and
 d) blocking unconverted epoxy groups on the PDAM beads.

In some embodiments, the process further comprises e) washing the PDAM beads with 0.1 M phosphate buffer and water.

In some embodiments, in step a) the cellulose beads are washed with 98% ethanol and distilled water. In some embodiments, in step b) the washed cellulose beads are incubated with a mixture of (±)-epichlorohydrin and 2.5 M NaOH. In some embodiments, in step c), the activated cellulose beads are suspended with a 20% solution of PAMAM dendrimer with an ethylenediamine core. In some embodiments, in step c) the suspending is conducted at 20-30° C. for 3-6 hours. In some embodiments, in step c) the suspending is conducted at 24° C. for 5 hours.

Also provided is a column comprising a PAMAM dendrimer affinity matrix (PDAM) described above. In some embodiments, the column is a PTFE column and the polyamidoamine dendrimer affinity matrix is sterilized.

In another aspect is provided an anti-DNA antibody affinity matrix prepared by a process comprising
 a) preparing activated agarose beads by crosslinking N-hydroxysuccinimide with agarose beads;
 b) washing the activated agarose beads with coupling buffer comprising NaHCO$_3$ and NaCl;
 c) adding an antibody against double stranded and single stranded DNA to the coupling buffer;
 d) incubating the coupling buffer comprising the antibody with the activated agarose beads to yield the anti-DNA antibody affinity matrix; and
 e) washing the anti-DNA antibody affinity matrix with coupling buffer and acetate buffer.

In some embodiments, the agarose beads have a mean size of 90 micrometers. In some embodiments, the coupling buffer comprises 0.2 M NaHCO$_3$ and 0.5 M NaCl and is at pH 8.3. In some embodiments, the antibody is a monoclonal antibody. In some embodiments, the antibody is a mouse antibody. In some embodiments, the washing step is performed at least three times. In some embodiments, the acetate buffer is 0.1 M acetate buffer at pH 4.0.

Also provided is a column comprising an anti-DNA antibody affinity matrix described above.

In some embodiments, the column is prepared by incubating the anti-DNA antibody affinity matrix with sterile Tris-HCl buffer. In some embodiments, the sterile Tris-HCl buffer is at pH 7.4.

In another aspect is provided an anti-nucleosome antibody affinity matrix (ANAM) prepared by a process comprising
 a) preparing activated agarose beads by crosslinking N-hydroxysuccinimide with agarose beads;
 b) washing the activated agarose beads with coupling buffer comprising NaHCO$_3$ and NaCl;
 c) adding to the coupling buffer an antibody that binds to nucleosomes, wherein the antibody is prepared in a MRL/Mp (−)+/+ mouse;
 d) incubating the coupling buffer comprising the antibody with the activated agarose beads to yield the anti-nucleosome antibody affinity matrix; and
 e) washing the anti-nucleosome antibody affinity matrix with coupling buffer and acetate buffer.

In some embodiments, the matrix binds to nucleosome bound circulating cfDNA, and the matrix does not bind to unbound cfDNA that includes dsDNA, ssDNA and oligonucleotides.

Also provided is a column comprising an anti-nucleosome antibody affinity matrix (ANAM) described above.

In yet another aspect is provided a DNA intercalating agent Hoechst 3342 affinity matrix prepared by a process comprising
 a) oxidizing cellulose beads;
 b) washing the oxidized cellulose beads;
 c) reacting the washed oxidized cellulose beads with a solution comprising Hoechst 33342 and N-(3-dimethylaminopropyl)-N'-ethyl carbodiimide (EDC) to yield Hoechst 33342 immobilized cellulose beads; and
 d) washing the Hoechst 33342 immobilized cellulose beads.

In some embodiments, in step a) the cellulose beads are oxidized with NaIO for 3-5 hours. In some embodiments, in step b) the oxidized cellulose beads are washed with 1 M sodium bicarbonate, 0.1 M hydrochloric acid and water. In some embodiments in step c), the solution is a pH buffered solution. In some embodiments in step d), the washing is conducted at least three times.

In another aspect is provided a hyper-branched poly-L-lysine affinity matrix (PLLAM) prepared by a process comprising a) dissolving L-lysine monohydrochloride in water and neutralizing with KOH to yield an L-lysine solution;
b) heating the L-lysine solution to yield a solution comprising hyper-branched poly-L-lysine;
c) removing the L-lysine and salt from the solution comprising hyper-branched poly-L-lysine;
d) fractionating the solution comprising hyper-branched poly-L-lysine to obtain a fraction comprising hyper-branched poly-L-lysine with an average molecular weight of 21,000 to 32,000; e) dialyzing and lyophilizing the fraction comprising hyper-branched poly-L-lysine with an average molecular weight of 21,000 to 32,000 to yield a lyophilizate;
f) dissolving the lyophilizate in distilled water and dialyzing against $NaHCO_3$ to yield a solution comprising HBPL; and
g) incubating the solution comprising hyper-branched poly-L-lysine with cyanogen bromide-activated Sepharose 4B suspended in $NaHCO_3$ to prepare hyper-branched poly-L-lysine affinity matrix.

In some embodiments, in step b) the L-lysine solution is heated to 150° C. for 48 hours under a stream of nitrogen. In some embodiments, in step c), the solution comprising hyper-branched poly-L-lysine is dialyzed against water. In some embodiments, in step d) the fractionation is conducted with a size exclusion column. In some embodiments, in step d), the fractionation is conducted with a gel filtration column.

Also provided is a column comprising a hyper-branched poly-L-lysine affinity matrix (PLLAM) described above.

In yet another aspect is provided a device configured to perform apheresis comprising one or more affinity columns comprising an affinity matrix and configured to remove substantially all types of cfDNA from the blood or plasma of a patient. In some embodiments, the device comprises two or more affinity columns in sequence. In some embodiments, the device further comprises a filtration cartridge. In some embodiments, the filtration cartridge has an inlet and an outlet. In some embodiments, one or more of the affinity columns has an inlet and an outlet.

In some embodiments, the device comprises two or more of the following affinity columns arranged in any sequence:
a) a column comprising a DNA binding protein (e.g., histone) affinity matrix;
b) a column comprising a lectin (e.g., *Galanthus nivalis* Lectin (GNA), *Narcissus Pseudonarcissus* Lectin (NPA), Conconavalin A, phytohemagluttanin, or cyanovirin) affinity matrix;
c) a column comprising a DNA binding polymer (e.g., a cationic polymer such as, e.g., amino terminated (—NH$_2$) PAMAM dendrimer, hyper-branched poly-L-lysine or hyper-branched polyethylenimine) affinity matrix;
d) a column comprising an anti-DNA antibody affinity matrix;
e) a column comprising a DNA intercalating agent (e.g., Hoechst 3342) affinity matrix;
f) a column comprising an anti-nucleosome antibody affinity matrix (ANAM); and
g) a column comprising an anti-histone antibody affinity matrix.

In some embodiments, the device comprises one of the following column combinations arranged in any order:
(a)(i) DNA intercalating agent Hoechst 33342 affinity column and (ii) anti-DNA antibody affinity column; or
(b) (i) anti-nucleosome antibody affinity matrix (ANAM) column and (ii) anti-DNA antibody affinity column; or
(c) (i) anti-nucleosome antibody affinity matrix (ANAM) column and (ii) polyamidoamine dendrimer affinity matrix (PDAM) column; or
(d) (i) anti-nucleosome antibody affinity matrix (ANAM) column and (ii) hyper-branched poly-L-lysine affinity matrix (PLLAM) column; or
(e) (i) anti-histone H2A antibody affinity column, (ii) lectin affinity column, and (iii) histone H1 affinity column or polyamidoamine dendrimer affinity matrix (PDAM) column or hyper-branched poly-L-lysine affinity matrix (PLLAM) column or DNA intercalating agent Hoechst 33342 affinity column.

In another aspect is provided an apheresis device comprising a filtration cartridge and one or more affinity columns having an inlet and an outlet, in which the device is capable of capturing substantially all types of cfDNA, including nucleosome bound cfDNA, exosome bound cfDNA and unbound cfDNA (including dsDNA, ssDNA and oligonucleotides), from blood or plasma of a patient.

In some embodiments, the device comprises two or more affinity columns in sequence. In some embodiments, the first affinity column in the sequence comprises a DNA binding polymer or a DNA intercalating agent.

In some embodiments, the device comprises a column comprising a histone affinity matrix upstream of, or before, a column comprising a lectin affinity matrix. In some embodiments, the device comprises a column comprising the histone affinity matrix upstream of, or before, a column comprising a lectin affinity matrix upstream of, or before, a column comprising a PAMAM affinity matrix. In some embodiments, the device comprises a column comprising an anti-DNA antibody affinity matrix upstream of, or before, a column comprising a Hoechst 3342 affinity matrix. In some embodiments, the device comprises a column comprising an anti-nucleosome antibody affinity matrix upstream of, or before, a column comprising a PAMAM affinity matrix.

In some embodiments, the apheresis device captures at least 30 mg of cfDNA per single apheresis procedure. In some embodiments, the affinity column comprises an immobilized moiety effective to capture one or more of nucleosome-bound cfDNA, exosome-bound cfDNA and unbound cfDNA, including dsDNA, ssDNA and oligonucleotides. In some embodiments, the immobilized moiety is selected from the group consisting of: DNA binding antibody, DNA intercalating agent, DNA binding protein, DNA binding polymer, lectin, anti-nucleosome antibody, and anti-histone antibody.

In some embodiments, the DNA binding protein is histone H1 (e.g., H1.3).

In some embodiments, the DNA binding polymer is a cationic polymer. In some embodiments, the cationic polymer is poly-L-lysine. In some embodiments, the poly-L-lysine is hyper-branched poly-L-lysine. In some embodiments, the cationic polymer is polyethylenimine.

In some embodiments, the polyethylenimine is hyper-branched polyethylenimine. In some embodiments, the cationic polymer is amino terminated (—NH$_2$) polyamidoamine (PAMAM) dendrimer.

In some embodiments of the above, the apheresis device comprises two sequential affinity columns, in which one column captures nucleosome bound DNA and exosome-bound DNA and another column captures unbound cfDNA including dsDNA, ssDNA and oligonucleotides. In some embodiments, the immobilized moiety is selected from the group consisting of a combination of two or more of the following moieties: DNA binding antibody, DNA intercalating agent, DNA binding protein, DNA binding polymer, lectin, anti-nucleosome antibody, or anti-histone antibody.

In another aspect is provided a method of reducing the level of cfDNA in the blood of a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides).

In some embodiments, the method is effective to treat one or more of multiorgan failure, a neurodegenerative disease (e.g., Alzheimer's disease), cancer, sepsis, septic kidney injury, irradiation induced toxicity (e.g., acute radiation syndrome), and chemotherapy-related toxicity.

In some embodiments, the patient has a disease selected from the group consisting of cancer, metastatic cancer, acute organ failure, organ infarct, hemorrhagic stroke, graft-versus-host-disease (GVHD), graft rejection, sepsis, systemic inflammatory response syndrome (SIRS), multiple organ dysfunction syndrome (MODS), irradiation induced toxicity (e.g., acute radiation syndrome), chemotherapy-related toxicity, traumatic injury, pro-inflammatory status in aged individuals, diabetes, atherosclerosis, neurodegenerative disease, autoimmune disease, eclampsia, infertility, coagulation disorder, and infection.

In some embodiments, the method is effective to treat a disorder in a patient, wherein the disorder is selected from cancer, metastatic cancer, acute organ failure, organ infarct (including myocardial infarction and ischemic stroke, hemorrhagic stroke, autoimmune disorders, graft-versus-host-disease (GVHD), graft rejection, sepsis, systemic inflammatory response syndrome (SIRS); multiple organ dysfunction syndrome (MODS); graft-versus-host-disease (GVHD), traumatic injury, proinflammatory status in aged individuals, diabetes, atherosclerosis, neurodegenerative disease, autoimmune disease, eclampsia, infertility, coagulation disorder, pregnancy-associated complications and infection. In some embodiments, the patient is in need of treatment of the disorder.

In yet another aspect is provided a method for treating multiple organ dysfunction syndrome (MODS) in a patient. The method comprises (a) performing an apheresis procedure comprising diverting blood or plasma from the patient into an apheresis device to produce purified blood or plasma; and (b) returning the purified blood or plasma with reduced levels of the cfDNA to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of MODS.

In another aspect is provided a method for treating a neurodegenerative disease in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of the neurodegenerative disease.

In another aspect is provided a method for treating Alzheimer's disease in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of Alzheimer's disease.

In another aspect is provided a method for treating cancer in a patient. The method comprises (a) performing an apheresis procedure comprising diverting blood or plasma from the patient into an apheresis device to produce purified blood or plasma with reduced levels of cfDNA; and (b) returning the purified blood to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of cancer.

In another aspect is provided a method for treating sepsis in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of sepsis.

In another aspect is provided a method for treating a kidney injury in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of the kidney injury.

In another aspect is provided a method for treating chemotherapy-related toxicity in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of chemotherapy-related toxicity.

In another aspect is provided a method for treating irradiation induced toxicity (e.g., acute radiation syndrome) in a patient. The method comprises (a) performing an apheresis procedure comprising diverting blood or plasma from the patient into an apheresis device to produce purified blood or plasma with reduced levels of cfDNA; and (b) returning the purified blood or plasma to the patient. The apheresis procedure reduces the level of substantially all types of cfDNA in the patient's blood, including nucleosome-bound cfDNA, exosome-bound cfDNA and unbound cfDNA (including dsDNA, ssDNA and oligonucleotides). In some embodiments, the patient is in need of treatment of irradiation induced toxicity.

In some embodiments of any of the above methods, the blood is diverted from the portal vein of the patient.

In some embodiments of the above, the purified blood has reduced levels of cfDNA as compared to the levels of cfDNA in the blood from the patient prior to the apheresis procedure.

In some embodiments, the purified blood has reduced levels of all of nucleosome-bound cfDNA, exosome-bound cfDNA and unbound cfDNA, including dsDNA, ssDNA and oligonucleotides. In some embodiments, the method further comprises periodically monitoring the level of the circulating cfDNA in the patient's blood, and continuing the apheresis procedure to reduce the circulating level of cfDNA by at least 25% before concluding the apheresis procedure. In some embodiments, the method further comprises periodically monitoring the level of the circulating cfDNA in the patient blood, and continuing the apheresis procedure on the patient to reduce the circulating levels of cfDNA by at least 50% before concluding the apheresis procedure. In some embodiments, the method further comprises periodically monitoring the level of the circulating cfDNA in the patient blood, and continuing the apheresis procedure on the patient to reduce the levels of circulating cfDNA by at least 75% before concluding the apheresis procedure.

In some embodiments of any of the above, at least 30 mg of cfDNA is removed from the blood from the patient during one or several sequential apheresis procedures.

In some embodiments of the above, the method steps are repeated, or undertaken on a schedule. The method steps may be conducted twice a day, every day, every two days, every three days, every four days, every five days, every six days, every week, every eight days, every nine days, every 10 days, every 11 days, every 12 days, etc. Samples of blood may be taken from the patient and tested for levels of cfDNA to assess the frequency of conducting the methods of treatment.

Arrangement of affinity columns in sequence can allow capturing of substantially all types of cfDNA, including nucleosome-bound cfDNA, exosome-bound cfDNA and unbound cfDNA (including dsDNA, ssDNA and oligonucleotides), from blood or plasma of a patient.

Various sequences are described herein and any sequence can be used. In some embodiments, the device comprises a column comprising a histone affinity matrix upstream of, or before, a column comprising a lectin affinity matrix. In some embodiments, the device comprises a column comprising the histone affinity matrix upstream of, or before, a column comprising a lectin affinity matrix upstream of, or before, a column comprising a polyamidoamine dendrimer affinity matrix (PDAM). In some embodiments, the device comprises a column comprising an anti-DNA antibody affinity matrix upstream of, or before, a column comprising a Hoechst 3342 affinity matrix. In some embodiments, the device comprises a column comprising an anti-nucleosome antibody affinity matrix (ANAM) upstream of, or before, a column comprising a polyamidoamine dendrimer affinity matrix (PDAM).

As part of the various aspects described throughout the application, is (a) performing an apheresis procedure comprising diverting blood or plasma from the patient into an apheresis device to produce purified blood or plasma; and (b) returning the purified blood or plasma with reduced levels of the cfDNA to the patient.

The apheresis device may comprise a histone affinity matrix. The histone affinity matrix may comprise recombinant human histone H1.3. The histone affinity matrix may be part of an affinity column. The beads used as support in a histone affinity matrix column may be cellulose beads that are oxidized with an oxidant before coupling with histone. The beads can be sepharose beads, for example. Alternatively, support of forms besides beads can be used (hollow fiber, membrane, tubing, etc.). Support of affinity matrix may be made from other organic and inorganic compounds known to one of skill in the art, for example, polyvinylpyrrolidone (PVP), polysulfone (PS), polyethersulfone (PES), polyarylethersulfone (PAES), polyacrylate, poly(methyl methacrylate) (PMMA), poly(glycidyl methacrylate) (PGMA), poly(hydroxy metacrylate), polystyrene (PS), polytetrafluoroethylene (PTFE), polyacrylamide, polyacrolein, acrylonitrile butadiene styrene (ABS), polyacrylonitrile (PAN), polyurethane (PU), eupergit®, polyethylene glycol (PEG), hyperfluorocarbon, agarose (i.e.cros-linked agarose), alginate, carrageenan, chitin, starch, cellulose, nitrocellulose, Sepharose®, glass, silica, kieselguhr, zirconia, alumina, iron oxide, porous carbon and mixtures and/or derivatives of said solid supports; and protonated and deprotonated forms of this separation material.

The beads may be coated with DNA-binding proteins. DNA-binding proteins such as histones or anti-DNA antibodies may be immobilized by chemically coupling it to a solid insoluble support matrix such as polysaccharide beads. For example, agarose beads are activated using cyanogen bromide and the cfDNA-capturing protein is incubated with the activated agarose to allow coupling to occur. The unconjugated material is removed by washing with buffer and the protein bound agarose is packed into the targeted apheresis device/affinity cartridge. There are many different methods of chemically coupling proteins to a variety of insoluble support matrixes. These and other matrix materials and methods of protein coupling known to those skilled in the art may be used in any of the methods and devices described herein.

For example, the attachment of a cfDNA-capturing molecule to a solid support can be through an amine, thiol, imide (i.e., water-soluble carbodiimide) or other chemical attachment method known to one of skill in the art to attach a polypeptide or oligonucleotide to a solid support.

The size of the beads can range from 30 to 200 microns, 40 to 180 microns, 45 to 165 microns, 60 to 150 microns, for example. Any number of oxidants may be used, such as sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modification of cellulose nanocrystals, Nanoscale, 2014, 6, 7764, DOI: 10.1039/c4nr01756k) Also, cellulose (or agarose) support can be oxidized by other compounds known to one of skill in the art, for example, chromic acid, chromium trioxide-pyridine, dimethylsulfoxide. (see, for example, Peng, L. et al. Evaluation of activation methods with cellulose beads for immunosorbent purification of immunoglobulins, J.Biotechnology, 5 (1987) 255-265). The oxidized beads are then incubated with a sufficiently purified and concentrated solution of histone protein, such as recombinant human histone H1.3. The reaction may be stopped and then washed with buffer to remove soluble protein contaminants. Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modifucation of cellulose nanocrystals, Nanoscale, 2014, 6, 7764, DOI: 10.1039/c4nr01756k. Also, cellulose (or agarose) support can be oxidized by other compounds known to one of skill in the art, for example, chromic acid, chromium trioxide-pyridine, dimethylsulfoxide. See, for example, Peng, L. et al. Evaluation of activation methods with cellulose beads for immunosorbent purification of immunoglobulins, J.Biotechnology, 5 (1987) 255-265).

The apheresis device may comprise a histone affinity matrix. The histone affinity matrix may comprise recombinant human histone H1.3. The histone affinity matrix may be part of an affinity column. The beads used in a histone affinity matrix column may be cellulose beads that are oxidized with an oxidant. The beads can be sepharose beads, for example. The beads may be coated with streptavidin. The size of the beads can range from 30 to 200 microns, 40 to 180 microns, 45 to 165 microns, 60 to 150 microns, for example. Any number of oxidants may be used, such as sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO). See, for example, Eyle, S. and Thielemans, W., Surface modification of cellulose nanocrystals, Nanoscale, 2014, 6, 7764, DOI: 10.1039/c4nr01756k) Also, cellulose (or agarose) support can be oxidized by other compounds known to one of skill in the art, for example: chromic acid, chromium trioxide-pyridine, dimethylsulfoxide. (See, e.g., Peng, L. et al. Evaluation of activation methods with cellulose beads for immunosorbent purification of immunoglobulins, J.Biotechnology, 1987, 5:255-265). The oxidized beads are then incubated with a sufficiently purified and concentrated solution of histone protein, such as recombinant human histone H1.3. The reaction may be stopped and then washed with buffer to remove soluble protein contaminants.

The histone affinity matrix is prepared by a process comprising
 a) oxidizing cellulose beads having a size between 100 and 250 micrometers to yield activated cellulose beads;
 b) washing the activated cellulose beads;
 c) preparing a concentrated solution of recombinant human histone H1.3;
 d) incubating the activated cellulose beads with the concentrated solution of recombinant human histone H1.3; and
 e) blocking any free CHO groups on the activated cellulose beads.

The above process may further comprise: f) washing the activated cellulose beads with buffer.

Any oxidant may be used in step a). One exemplary oxidant is NaIO. Any manner of washing can be undertaken in step b). For example, the activated cellulose beads are washed with sodium bicarbonate, hydrochloric acid and water. Dialysis or other methods may be used in step c). For example, a solution of recombinant human histone H1.3 is dialyzed and the dialyzed solution is concentrated in 0.1 M $NaHCO_3$ at pH 7-9, or at pH 8. In step d), the incubation may be performed for 3-5 hours at 15-30° C., or for 4 hours at room temperature. In step e) the blocking step comprises adding 1 M ethanolamine to the activated cellulose beads and reacting for 30 minutes to 2 hours at 15-30° C. In step f) the activated cellulose beads, may be washed with TBS buffer.

The beads may be loaded onto a column, such as, e.g., a polytetraflouroethylene (PTFE) column. Other exemplary columns may have a wall made of polycarbonate, polyethylene, polyvinylchloride, polypropylene, polyethersulfone, polyester, or other polymer material approved by FDA or EMEA for manufacturing of devices for extracorporeal treating of blood or blood component.

The column, or cartridge device, can be also made of material that is nontoxic and which provides rigid support to the affinity matrix within. Typically, the material will be a plastic composition such as polycarbonate, polyethylene, polyvinylchloride, polypropylene, polyethersulfone, polyester, polystyrene, or other similar material approved by the regulators such as FDA or EMEA for manufacturing of devices for extracorporeal treating of blood or blood component. In some embodiments, there is an inside filter at the bottom of the column (cartridge) to prevent the affinity matrix from leaving the device. In some embodiments, there is also an inside filter at the top of the device to contain the affinity matrix within the device. In some embodiments, these filters are composed of plastic and/or cellulosic material and have pores that will allow through passage of fluid such as plasma, but not particulate material such as affinity matrix.

In preparing a histone affinity matrix column, the histone affinity matrix may be loaded to at least 50%, 60%, 70%, 75%, 80%, 85%, or 90% column volume. PBS, particularly cold PBS may be used to equilibrate the column. Other suitable buffers may also be used to equilibrate the column.

The apheresis device may comprise a lectin affinity matrix. Non-limiting examples of useful lectins include, e.g., *Galanthus nivalis* (snowdrop) Lectin (GNA), *Narcissus Pseudonarcissus* (Daffodil) Lectin (NPA), Conconavalin A, phytohemagluttanin, and cyanovirin. In one embodiment, a lectin can be coupled to an agarose affinity matrix by incubating overnight at a neutral to slightly alkaline pH. After such incubation, extensive washing with buffer at a pH of near 7.0 to 7.5 may be undertaken to remove the unbound lectin.

A lectin affinity matrix may be prepared according to a process comprising
 a) reacting lectin with activated agarose beads to yield lectin-coupled agarose; and
 b) washing the lectin-coupled agarose with buffer.

The apheresis device may comprise a polyamidoamine (PAMAM) dendrimer affinity matrix (PDAM) or polypropyleneimine (PPI) dendrimer affinity matrix. See, e.g., Kaur et al., J Nanopart Res., 2016, 18:146. Dendrimers are unique synthetic polymers of nanometer dimensions with a highly branched structure and globular shape. Among dendrimers, polyamidoamine (PAMAM) have received most attention as potential transfection agents for gene delivery, because these macromolecules bind DNA at physiological pH. PAMAM dendrimers consist of an alkyl-diamine core and tertiary amine branches. They are available in ten generations (G0-10) with 5 different core types and 10 functional surface groups. DNA and polyamidamine (PAMAM) dendrimers form complexes on the basis of the electrostatic interactions between negatively charged phosphate groups of the nucleic acid and protonated (positively charged) amino groups of the polymers. Formation of high molecular weight and high-density complexes depend mainly on the DNA concentration, with enhancement by increasing the dendrimer- DNA charge ratio. (Shcharbin, D. et al., Practical Guide to Studying Dendrimers. Book, iSmithers Rapra Publishing: Shawbury, Shrewsbury, Shropshire, U K, 2010. 120 p. ISBN: 978-1-84735-444-0.)

The PAMAM dendrimer affinity matrix prepared by a process comprising
  a) washing cellulose beads with ethanol and water;
  b) incubating the washed cellulose beads with (±)-epichlorohydrin and NaOH to yield activated cellulose beads;
  c) reacting the activated cellulose beads with PAMAM dendrimer to yield PAMAM beads and removing PAMAM dendrimer that did not react with the activated cellulose beads; and
  d) blocking unconverted epoxy groups on the PAMAM beads.

The beads may be loaded onto a column, such as a polytetraflouroethylene (PTFE) column. Other exemplary columns may have a wall made of polycarbonate, polyethylene, polyvinylchloride, polypropylene, polyethersulfone, polyester, or other polymer material approved by FDA or EMEA for manufacturing of devices for extracorporeal treating of blood or blood component.

An apheresis device comprising a PAMAM dendrimer affinity matrix may be more effective at removing cfDNA, or alternatively may more completely remove cfDNA, or alternatively may remove a greater overall amount of cfDNA in a particular blood sample, than using an apheresis device comprising a histone affinity matrix and a lectin affinity matrix.

In certain embodiments, the apheresis device may comprise all of a PAMAM dendrimer affinity matrix, a histone affinity matrix and a lectin affinity matrix.

The apheresis device may comprise an anti-DNA antibody affinity matrix. Antibodies to DNA constitute a subgroup of antinuclear antibodies that bind single-stranded DNA, double-stranded DNA, or both (anti-ds+ss DNA antibody). They may be, e.g., IgM antibodies or any of the subclasses of IgG antibodies. Antibodies that bind exclusively to single-stranded DNA can bind its component bases, nucleosides, nucleotides, oligonucleotides, and ribose-phosphate backbone, all of which are exposed in single strands of DNA. Antibodies that bind double-stranded DNA can bind to the ribose-phosphate backbone, base pairs (deoxyguanosine-deoxycytidine and deoxyadenosine-deoxythymidine), or particular conformations of the double helix (Bevra Hannahs Hahn, Antibodies to DNA. N Engl J Med 1998; 338:1359-1368). Antibodies to DNA might also bind DNA containing supramolecular structures like nucleosomes and chromatin.

The anti-DNA antibody affinity matrix can be prepared by activating agarose beads, such as with N-hydroxysuccinimide (NHS). The activated beads can then be incubated with an antibody or other reagent that has affinity to DNA. The excess antibodies/reagents are then removed by washing.

An anti-nucleosome antibody affinity matrix (ANAM) prepared by a process comprising
  a) preparing activated agarose beads by crosslinking N-hydroxysuccinimide with agarose beads;
  b) washing the activated agarose beads with coupling buffer comprising $NaHCO_3$ and NaCl;
  c) adding to the coupling buffer an antibody that binds to nucleosomes, wherein the antibody is prepared in a MRL/Mp (−)+/+ mouse;
  d) incubating the coupling buffer comprising the antibody with the activated agarose beads to yield the anti-nucleosome antibody affinity matrix; and
  e) washing the anti-nucleosome antibody affinity matrix with coupling buffer and acetate buffer.

The apheresis device may comprise a DNA intercalator affinity matrix. There are several ways molecules can interact with DNA. Ligands may interact with DNA by covalently binding, electrostatically binding, or intercalating. Intercalation occurs when ligands of an appropriate size and chemical nature fit themselves in between base pairs of DNA. DNA-binding agents tend to interact noncovalently with the host DNA molecule through two general modes: (i) Threading Intercalation in a groove-bound fashion stabilized by a mixture of hydrophobic, electrostatic, and hydrogen-bonding interactions and (ii) Classical intercalation through an intercalative association in which a planar, heteroaromatic moiety slides between the DNA base pairs. Intercalative binding, the most commonly studied, is the noncovalent stacking interaction resulting from the insertion of a planar heterocyclic aromatic ring between the base pairs of the DNA double helix. See nptel.ac.in/courses/104103018/35. Hoechst 33342 is a bis-benzimide derivative that binds to AT-rich sequences in the minor grove of double-stranded DNA. The heterocyclic moiety in this dye is important for efficiently interacting with the DNA double helix, thus making the Hoechst-DNA complex more stable.

The DNA intercalator affinity matrix may be prepared by oxidizing (activating) beads, such as cellulose beads (support) reacting with a compound (linker), such as N-(3-dimethylaminopropyl)-N'-ethyl carbodiimide (EDC) that link the DNA-intercalator (DNA-binding moiety, i.e. Hoechst 33342) with support surface. The beads are then washed.

A Hoechst 3342 affinity matrix prepared by a process comprising
  a) oxidizing cellulose beads;
  b) washing the oxidized cellulose beads;
  c) reacting the washed oxidized cellulose beads with a solution comprising Hoechst 33342 and N-(3-dimethylaminopropyl)-N'-ethyl carbodiimide (EDC) to yield Hoechst 33342 immobilized cellulose beads; and
  d) washing the Hoechst 33342 immobilized cellulose beads.

The apheresis device may comprise a hyperbranched poly-L-lysine affinity matrix. A hyperbranched poly-L-lysine affinity matrix may be prepared by a process comprising
  a) dissolving L-lysine monohydrochloride in water and neutralizing with KOH to yield an L-lysine solution;
  b) heating the L-lysine solution to yield a solution comprising poly-L-lysine;
  c) removing the L-lysine and salt from the solution comprising poly-L-lysine;
  d) fractionating the solution comprising poly-L-lysine to obtain a fraction comprising poly-L-lysine with an average molecular weight of 21,000 to 32,000;
  e) dialyzing and lyophilizing the fraction comprising poly-L-lysine with an average molecular weight of 21,000 to 32,000 to yield a lyophilizate;
  f) dissolving the lyophilizate in distilled water and dialyzing against $NaHCO_3$ to yield a solution comprising HBPL; and
  g) incubating the solution comprising HBPL with cyanogen bromide-activated Sepharose 4B suspended in $NaHCO_3$.

In certain embodiments, the apheresis device may comprise all of, or any number of the following: a DNA intercalator affinity matrix, a Hoechst 33342 affinity matrix, an anti-DNA affinity matrix, a PAMAM affinity matrix, a histone affinity matrix, a lectin affinity matrix, and a poly-L-lysine affinity matrix.

Various apheresis procedures and methods of treatment are described throughout the application. Various methods and procedures comprise (a) performing an apheresis procedure comprising diverting blood or plasma from the patient into an apheresis device to produce purified blood or plasma; and (b) returning the purified blood or plasma with reduced levels of the cfDNA to the patient. Any vein may be selected for optimal diversion of the blood. For example, the blood may be diverted from the portal vein of the patient. Alternatively, the blood may be diverted from the femoral vein or the jugular vein of the patient.

In various embodiments of treatment, an apheresis procedure may be carried out more than once, or even twice, for example on day 1 and on day 3. If treating kidney injury, the level of kidney injury can be assessed by measuring serum creatinine and blood urea nitrogen (BUN)levels with Roche Reflotron Plus (Roche Diagnostics) before each apheresis procedure.

Circulating cfDNA can be extracted from plasma samples with conventional THP (Triton-Heat-Phenol) method (Breitbach et al., PLoS ONE, 2014, 9(3):e87838). Extracted cfDNA may be quantified with various assays, such as, e.g., the PicoGreen assay (Molecular Probes, Netherlands) following the manufacturer's instructions. For visualization of cfDNA in agarose gel as described in the examples, below, well known DNA dyes can be used, including, e.g., ethidium bromide (Sigma-Aldrich), Diamond™ Nucleic Acid Dye (Promega), SYBR® Gold Nucleic Acid Gel Stain (Molecular Probes). The dyes can be used as either a gel stain, a precasting agent or can be preloaded directly into sample loading buffer.

In various embodiments, performing an apheresis procedure further comprises separating the blood into plasma. The plasma portion may then be diverted to one or more affinity matrices so as to remove cfDNA.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Preparation of Histone H1 Affinity Matrix and Affinity Column

The histone H1 affinity matrix and affinity column were prepared as follows: cellulose beads (bead size of 100-250 micrometers, Sigma-Aldrich) were oxidized with sodium metaperiodate. To accomplish this, an aqueous suspension of the beads (3 g, 5 mL) and $NaIO_4$ (0.1 g, 0.5 mmol) in 10 mL of water was shaken at room temperature for 4 h. The activated beads were collected and washed with 1 M sodium bicarbonate, 0.1 M hydrochloric acid and 200 mL of water. A solution of recombinant human histone H1.3 (≥98% purity, Institute of Bioorganic Chemistry, Moscow) was dialyzed and concentrated (10 mL; 5 mg/mL) in 0.1 M $NaHCO_3$ (pH 8). Then the solution was incubated with oxidized beads (5 ml) at room temperature for 4 h with stirring. After the incubation, 1 M ethanolamine (1.5 mL) was added to the activated beads suspension (15 ml) to block the free CHO groups; the reaction continued for 1 h at room temperature. The resulting cellulose beads with immobilized histone H1 were washed three times with TBS buffer to remove soluble protein contaminants and to provide histone H1 affinity matrix. Polycarbonate columns of 4 mL-30 mL volume were loaded (to 70-90% of the volume) with the cellulose matrix with immobilized histone H1.

Example 2: Purification of the Blood of Cancer Patient from Different Types of Circulating cfDNA Separation of particle bound type of cfDNA (i.e. nucleosome-bound cfDNA and exosome-bound cfDNA) from unbound circulating cfDNA was performed as follows: plasma from a cancer patient with advanced gastric adenocarcinoma and multiple metastases in lungs and liver (T4N2M1) was prepared by collecting blood into citrate-treated tubes and centrifuging for 10 minutes at 2,000 g using a refrigerated centrifuge and collection of supernatant.

The nucleosome-bound cfDNA and exosome-bound cfDNA were removed using two sequential affinity columns containing anti-histone antibody based affinity matrix and lectin based affinity matrix as described respectively in WO2007/049286A1 and U.S. Pat. No. 9,364,601.

Briefly, an anti-histone antibody affinity matrix and a column were prepared as follows: 0.5 mL (1 volume) of streptavidin coated sepharose beads (average bead size: 45 to 165 microns, Pierce Biotechnology, USA) were packed on to a 1.3 volume (1.3 mL) polystyrene column above glass wool. The column was equilibrated with 2 mL (4 volumes) of PBS. 1 mL (volume) of 100 µg/mL solution of biotinylated anti-histone antibodies (H2A.X; Santa Cruz Biotechnologies) were added to the column and allowed to enter the gel bed. The bottom and top caps were sequentially replaced and incubated for 2 hours at room temperature. Following incubation, the column was washed with 2 mL (4 volumes) of cold phosphate buffered saline (PBS).

Lectin affinity matrix was prepared as follows: 2 mL (1 volume) of Lectin from *Galanthus nivalis* (snowdrop), i.e., GNA (Sigma-Aldrich) solution at a concentration of 10 mg/mL in 0.1M $NaHCO_3$, pH 9.5 was added to 2 mL (1 volume) of CNBr activated agarose beads (Cyanogen bromide-activated-Sepharose 6 MB, 6% agarose, 200-300 µm diameter macrobeads, Sigma-Aldrich) and allowed to react overnight in the cold at pH 7.4-8.0. When the reaction was complete, the lectin coupled agarose was washed extensively with sterile cold phosphate buffered saline (PBS) at pH 7.2-7.4. The prepared lectin affinity matrix was transferred to a 0.6×6 cm polystyrene column.

For the purification from nucleosome bound cfDNA 1.0 mL of plasma was applied to the first affinity column (comprising anti-histone H2A antibody affinity matrix) and allowed to flow through. Then the plasma was applied to the second affinity (exosome binding) column (comprising lectin [GNA] affinity matrix) and allowed to flow through.

Alternatively, the same amount of the patient plasma was allowed to flow through a single histone H1 affinity column prepared as described in Example 1 (cellulose beads coupled with immobilized histone H1.3).

All plasma samples were analyzed by gel electrophoresis with fluorescent DNA dye staining prior to apheresis and following the completion of apheresis.

The electrophoretic profile of circulating cfDNA from plasma of the cancer patient prior removal of nucleosome bound DNA and exosomes (Lane A), following sequential affinity purification with anti-histone H2A antibody and lectin affinity columns (Lane B) and following affinity purification with histone H1.3 affinity column (Lane C) is presented in FIG. 1.

Even though nucleosome bound circulating cfDNA and exosomes were removed from plasma, the sample shown in the middle lane still contained significant amounts of circulating cfDNA visualized within a molecular range of 100-1000 base pairs. As shown in the right lane, no DNA was visualized in the sample following passage through histone H1.3 affinity column. Thus apheresis/purification of patient plasma through affinity matrix containing DNA binding protein (histone H1.3) can remove a large proportion of, nearly all of, or all of, nucleosome-bound cfDNA, exosome-bound cfDNA and unbound cfDNA including dsDNA, ssDNA and oligonucleotides from patient blood.

Example 3: Circulating cfDNA Purified from Nucleosome Bound DNA and Exosomes Promotes Tumor Growth 60 mL of plasma was collected from a metastatic non-small-cell lung carcinoma patient (NSCLC T3N2M+) over a few consecutive days and purified from circulating nucleosome bound cfDNA and from exosomes using anti-histone H2.A antibody and lectin affinity columns, consequently, as described in Example 2 (affinity matrix with anti-histone antibodies and affinity matrix with lectin from *Galanthus nivalis* (snowdrop)). For affinity column preparation, polycarbonate 2.0×7.0 cm columns were used. Each was loaded to 70-80% of the column volume with the corresponding matrix. The remaining circulating cfDNA was extracted from purified plasma using classic phenol chloroform extraction and ethanol precipitation (Stirling, D. et al, DNA extraction from plasma and serum, In: Methods in Molecular Biology, vol. 226: PCR Protocols, Second Edition, Ed. by J. M. C. Bartlett and D. Stirling, Humana Press Inc., Totowa, N J, 2003, 556 pages). Dry extracted cfDNA was stored at −70° C. The total amount of residual DNA recovered from patient plasma following purification from nucleosome and exosome bound circulating cfDNA was 9.7 μg. The cfDNA was redissolved in PBS and used for animal experiments as described below.

The effect on tumor growth of cfDNA which was not bound to nucleosome and exosome was tested using Panc02/C57/BL6 orthotopic model (Jiang Y-J, Lee C-L, Wang Q, et al. Establishment of an orthotopic pancreatic cancer mouse model. World Journal of Gastroenterology: WJG. 2014; 20(28):9476-9485). 1×10⁶ Panc02 cells suspended in ice-cold Martigel were injected to pancreas tail of each animal (Day 0). 24 tumor bearing mice were divided into 3 groups of 8 mice each. Control group mice were given single daily injections of PBS (100 μL; retro-orbital venous sinus) for 10 days: from Day 10 to Day 20. Group 1 mice were given daily injections of 100 ng cancer patient cfDNA purified as described above and mice of group 2 were given with 100 ng UltraPure™ Salmon Sperm DNA (Life Technologies) with an average size of ≤2,000 base pairs (as non-specific control) using same schedule and technique.

Table 1 below summarizes the effects of DNA injections on tumor weight in treated animals versus the control group. Tumor weight was measured at the study termination on Day 23.

TABLE 1

| Group | N | Test Material | Tumor Weight (g) Day 23, Median ± SD |
|---|---|---|---|
| Control | 8 | Vehicle (PBS) | 1.37 ± 0.64 |
| Group I | 8 | cfDNA from NSCLC T3N2M+ patient plasma purified from nucleosome and exosome bound cfDNA | 2.53 ± 0.35 |
| Group II | 8 | UltraPure ™ Salmon Sperm DNA | 1.11 ± 0.10 |

Figure 2A:
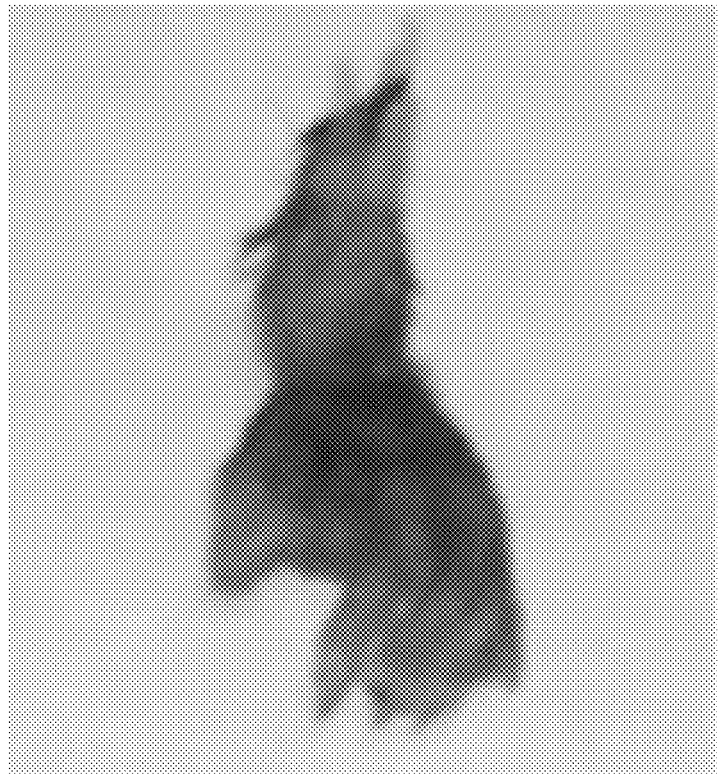
FIGS. 2A and 2B show tumors excised from mice treated with DNA according to Example 3, where blood was purified with an affinity matrix with anti-histone antibodies and an affinity matrix with lectin from *Galanthus nivalis* (snowdrop).
Figure 2B:
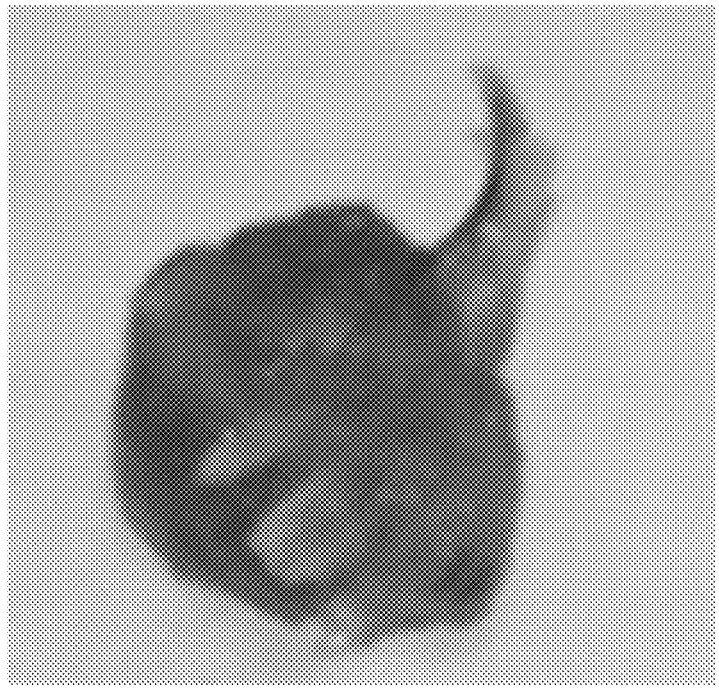

FIG. 2A shows tumors excised from control group mice. FIG. 2B shows tumors excised from mice treated with cfDNA from an NSCLC T3N2M+ patient purified from nucleosome and exosome bound circulating cfDNA. Tumors from the control group were much smaller, dense, well separated from adjacent organs and do not have necrosis and hemorrhages.

The circulating cfDNA from cancer patient plasma purified from nucleosome and exosome bound circulating cfDNA retained significant tumorigenic properties. Thus, it may be beneficial to reduce levels all of nucleosome-bound cfDNA, exosome-bound cfDNA and unbound cfDNA including dsDNA, ssDNA and oligonucleotides.

Example 4: Preparation of Polyamidoamine Dendrimer Affinity Matrix and Affinity Column PAMAM dendrimer affinity matrix (PDAM) and columns which contain PDAM were prepared according to Wang (Wang, Y., et al., New method for the preparation of adsorbent with high adsorption capacity, Chinese Science Bulletin 2005, Vol. 50, No. 21, pp 2432-2435) as follows. Cellulose beads (Macroporous Bead Cellulose MT 500, particle size 100-250 μm, Iontosorb, Czech Republic) were washed twice with 98% ethanol and distilled water. 1 gram of the beads was incubated with a mixture of 1.0 ml (±)-Epichlorohydrin (Sigma-Aldrich) and 3.0 ml of 2.5 M NaOH. The activating reaction was performed at 40° C. for 2.5 h in a shaker. Activated beads were washed thoroughly with distilled water. The epoxy content of the resins was determined as about 0.31 mmol/g of dry beads by titration of sodium thiosulfate with hydrogen chloride. 4.0 ml of prepared wet activated cellulose beads was suspended with 9.0 ml of 20% solution of amino terminated (—NH₂) PAMAM dendrimer (ethylenediamine core, generation 3.0, Sigma-Alrich) solution and shaken at 24° C. for 5 h. After the modification, unreacted PAMAM was removed by washing with distilled water and the remaining unconverted epoxy groups on the beads were blocked by reacting with ethylamine. The functionalized affinity matrix was then washed with 0.1 M phosphate buffer and MilliQ water. 2.0-20.0 mL of prepared affinity matrix were placed in pyrogen free polytetraflouroethylene (PTFE) (0.5-3.0) cm×(1.0-10.0) cm column (to load of 70-90% of column volume). The prepared affinity column was sterilized by autoclaving at 121° C. for 30 min.

Example 5: Purification of Blood Plasma of Cancer Patient and Stroke Patient from Different Types of Circulating cfDNA 1.0 ml aliquots of plasma samples from both an ischemic stroke patient (24 hours since stroke onset) and a cancer patient with advanced gastric adenocarcinoma with multiple metastases in lungs and liver (T4N2M1) were subsequently purified through both anti-histone H2A antibody and lectin affinity columns, as described in Example 2 (affinity matrix with anti-histone H2A antibodies and affinity matrix with lectin from *Galanthus nivalis* (snowdrop)), or through a polyamidoamine dendrimer affinity 0.6×10.0 cm column alone prepared as described in Example 4 (affinity matrix of cellulose beads coupled with PAMAM dendrimer).

All plasma samples were analyzed by gel electrophoresis with fluorescent DNA dye staining prior to purification and following purification completion.

Figure 3:
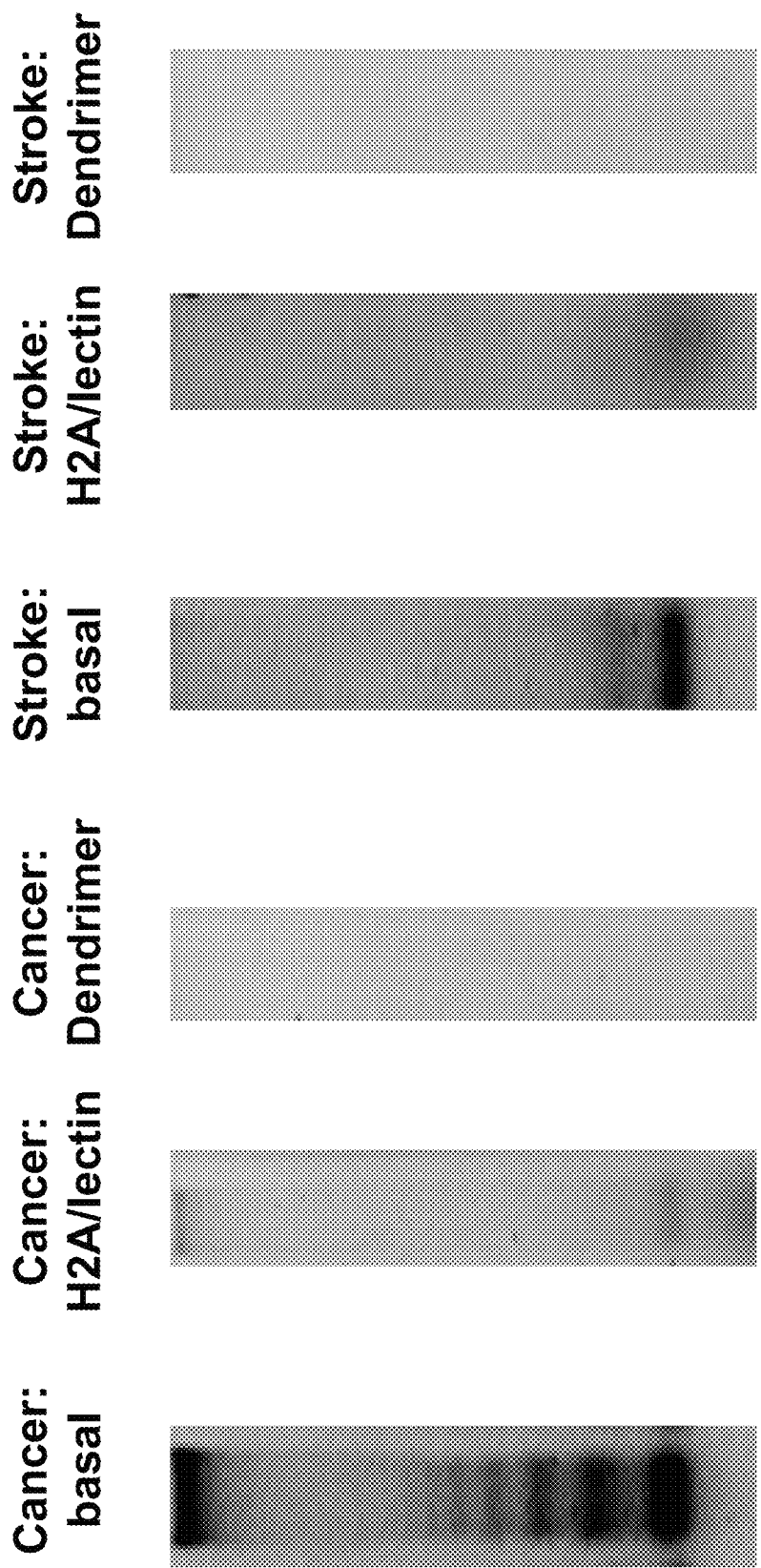
FIG. 3 shows an electrophoretic profile of circulating cfDNA from plasma of a metastatic cancer patient and a stroke patient.

The electrophoretic profile of circulating cfDNA from plasma of these patients prior to removal of nucleosome bound cfDNA and exosomes, following affinity apheresis with anti-histone antibody and lectin affinity columns, and following affinity purification with polyamidoamine dendrimer affinity column are presented in FIG. 3.

Consequent purification of plasma of the cancer patient with anti-histone antibody- and lectin affinity columns removed the majority of particle-bound circulating cfDNA; however, a visible amount of nucleosome bound circulating cfDNA and circulating cfDNA of mononucleosomal size and subnucleosomal size (~below 147 base pairs in length) remained in plasma. Plasma purification with a polyamidoamine (PAMAM) dendrimer affinity column lead to complete elimination of circulating cfDNA from plasma of the cancer patient. In a stroke patient, affinity purification with polyamidoamine dendrimer affinity column (used as a single step) lead to sufficient elimination of substantially all types of circulating cfDNA from the plasma such that they were undetectable.

Thus, the patient blood plasma can be purified from substantially all types of cfDNA, including nucleosome-bound cfDNA, exosome-bound cfDNA and unbound cfDNA (including dsDNA, ssDNA and oligonucleotide) with an affinity matrix containing a DNA binding polymer.

Example 6: cfDNA of Blood Plasma Purified from Nucleosome Bound DNA and Exosomes has Procoagulant Activity U.S. Pat. No. 9,642,822 discloses that high molecular weight circulating nucleosome bound cfDNA in the form of neutrophil NETs has procoagulant activity in patients with advanced cancer and acute vascular events. The blood plasma of patient with stroke (24 hours since onset) and cancer patient with advanced gastric adenocarcinoma with multiple metastasis in lungs and liver (T4N2M1) was sampled and purified consequently through both lectin- and anti-histone antibody affinity columns (prepared as described in Example 2 (affinity matrix with anti-histone H2A antibodies and affinity matrix with lectin from *Galanthus nivalis* [snowdrop]) or through polyamidoamine dendrimer affinity 1.0×5.0 cm column (prepared as described in Example 4). Purified and untreated plasma samples were further defibrinated by spinning at 3,000 g for 20 min and filtering through a 0.22 µm filter. Samples were aliquoted into 1.0 mL plastic tubes, shaken in a water bath at 50° C. for 25 min and centrifuged at 10,000 g (10 min). The supernatants were stored at −80° C. and then tested in a thrombin generation assay as follows: a mixture of 25 µL of diluted (1:9) thromboplastin (Sigma), 25 µL of 0.9% NaCl, and 50 µL of 1:1 dilution of defibrinated plasma (all reagents were diluted in 0.9% NaCl).

All reagents in the thrombin generation assay were diluted in 0.9% NaCl. A mixture of 25 µl of thromboplastin, 25 µL of 0.9% NaCl, and 50 µL of 1:1 dilution of defibrinated plasma to be tested were added to wells of a microtiter plate and prewarmed to 37° C. for 10 min. Then 50 µL of 1 mM spectrozyme, a chromogenic substrate for thrombin, and 50 µL of 30 mM calcium chloride were added sequentially. The plates were read out in an automated enzyme-linked immunosorbent assay plate reader (Victor, Perkin Elmer) at 1000 s and 405 nm at room temperature. All measurements were done in triplicate. In this test OD value is proportional of procoagulant activity of plasma (thrombin generation).

TABLE 2

| Plasma sample | OD (405 nm) measured at 1000 sec Mean ± SD |
|---|---|
| Cancer patient, untreated | 0.87 ± 0.12 |
| Cancer patient, purified with lectin- and anti-histone antibody affinity matrices/columns | 0.56 ± 0.08 |
| Cancer patient, purified with polyamidoamine dendrimer affinity matrix/column | 0.23 ± 0.07 |
| Stroke patient, untreated | 1.17 ± 0.4 |
| Stroke patient, purified with lectin- and anti-histone antibody affinity matrices/columns | 0.81 ± 0.4 |
| Stroke patient, purified with polyamidoamine dendrimer affinity matrix/column | 0.31 ± 0.3 |
| Healthy donor | 0.13 ± 0.2 |

The results are shown in Table 2. Thus, not only nucleosome- and exosome-bound circulating cfDNA but also unbound cfDNA has procoagulant activity in cancer and acute vascular events. Thus reducing the levels of all types of cfDNA, including nucleosome-bound cfDNA, exosome-bound cfDNA and unbound cfDNA (including dsDNA, ssDNA and oligonucleotides) is beneficial.

Example 7: Preparation of Anti-DNA Antibody Affinity Matrix and Column

Anti-DNA antibody affinity matrix and affinity column were prepared as follows: 5 mL of spherical beads from highly cross-linked N-hydroxysuccinimide (NHS) activated 4% agarose, mean beads size of 90 micrometers (NHS-activated Sepharose 4 Fast Flow, GE Healthcare Life Sciences) were used. The activated matrix was washed twice with cold (2-4° C.) coupling buffer (0.2 M NaHCO$_3$, 0.5 M NaCl, pH 8.3). 1000 µg of high affinity mouse monoclonal IgM Anti-ds+ss DNA antibody ([49/4A1], ab35576, Abcam) were dialyzed against coupling buffer and then coupled according to the manufacturer's procedure to NHS activated Sepharose. Three cycles of washing with coupling buffer followed by 0.1 M acetate buffer (pH 4.0) were used to remove the excess of unbound anti-DNA antibodies. 4 mL of washed affinity matrix was poured to 5 mL column and affinity column was equilibrated in sterile Tris-HCl buffer (pH 7.4).

Example 8: Preparation of DNA Intercalator Affinity Matrix and Column

Hoechst 33342 affinity matrix and affinity column were prepared as follows: cellulose beads (bead size of 100-250 micrometers, Sigma-Aldrich) were oxidized with sodium metaperiodate. For this aqueous suspension of the beads (3 g, 5 mL) and NaIO, (0.1 g, 0.5 mmoL) in 10 mL of water were shaken at room temperature for 4 h. The activated beads were collected and washed with 1 M sodium bicarbonate, 0.1 M hydrochloric acid and 200 ml of water. 450 mg of activated cellulose beads were mixed with 1000 mL of a pH buffered solution containing 0.047 mg/mL of Hoechst 33342 (Sigma-Aldrich), and 0.4 mg/mL of N-(3-dimethylaminopropyl)-N'-ethyl carbodiimide (EDC) and reacted at a constant vortex rate for 1 h at 32° C. The beads with immobilized Hoechst 33342 were washed three times with deionized water to remove the unreacted dye. The prepared DNA-intercalator affinity matrix was placed into a 4 mL volume plastic (polycarbonate) column. The column was stored at 4° C.

Example 9: Separation of Different Types of Circulating cfDNA from the Blood of Patient with Systemic Inflammatory Response Syndrome (SIRS) and Multiple Organ Dysfunction Syndrome (MODS)

Plasma was sampled from the patient admitted to the intensive care unit (ICU) diagnosed with systemic inflammatory response syndrome (SIRS) with multiorgan failure (multiple organ dysfunction syndrome, MODS) secondary to acute pancreatitis. Therapeutic plasma exchange was performed as a rescue therapy. Aliquots of 1 mL of discharged patient plasma was purified through both lectin and anti-histone antibody affinity columns as described in Example 2 (affinity matrix with anti-histone antibodies and affinity matrix with lectin from *Galanthus nivalis* (snowdrop)) or through a DNA-intercalator affinity column as described in Example 8 (cellulose beads coupled with Hoechst 33342, a DNA intercalator affinity matrix). All plasma samples were analyzed by gel electrophoresis with fluorescent DNA dye staining prior to the purification and following the purification.

Figure 4:
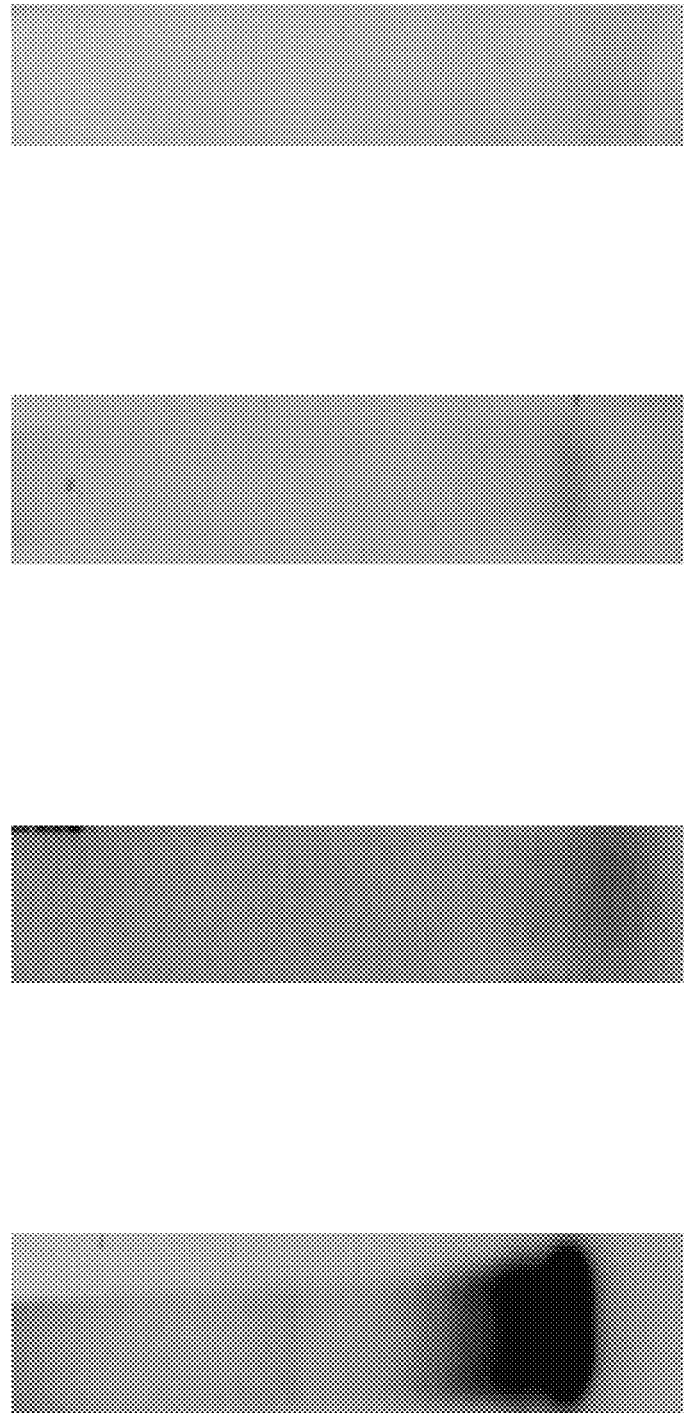
FIG. 4 shows an electrophoretic profile of circulating cfDNA from plasma of patient with systemic inflammatory response syndrome (SIRS) and multiple dysfunction syndrome (MODS).

As shown in FIG. 4, plasma of the SIRS patient contained significant amounts of circulating cfDNA, which gave a strong fluorescent signal following staining with fluorescent DNA dye. Affinity purification with anti-histone antibody and lectin affinity columns removed nucleosome bound circulating cfDNA; however a certain amount of nucleosome-bound circulating cfDNA and circulating subnucleosomal cfDNA (~below 147 base pairs in length) remained in plasma. Affinity purification with Hoechst 33342 affinity column led to elimination of circulating subnucleosomal cfDNA but a certain amount of nucleosome-bound circulating cfDNA was still present. The inventors therefore tested sequential purification with different columns: 1 ml aliquot of the patient plasma was purified sequentially through Hoechst 33342 affinity column followed by anti-dsDNA antibody affinity column in a manner described in Example 2 for sequential use of anti-histone antibody affinity and lectin affinity columns. Plasma was further checked with by gel electrophoresis with fluorescent DNA dye staining and no circulating cfDNA was detected.

Thus purification through affinity matrix containing two affinity matrixes of present invention can remove substantially all types of cfDNA in the patient's blood, including nucleosome-bound cfDNA, exosome-bound cfDNA and unbound cfDNA (including dsDNA, ssDNA and oligonucleotides), from blood or plasma from patient body.

Example 10: Circulating cfDNA of Plasma Purified from Nucleosome Bound DNA and Exosomes has Proinflammatory Activity and Contribute to Organ Dysfunction in Sepsis Plasma was sampled from the patient admitted to the intensive care unit (ICU) diagnosed with systemic inflammatory response syndrome with multiple organ dysfunction syndrome (MODS) secondary to acute pancreatitis. Therapeutic plasma exchange was performed as a rescue therapy. 100 mL of discharged patient plasma was purified through both lectin and anti-histone antibody affinity columns (as described in Example 2, i.e. affinity matrix with anti-histone antibodies and affinity matrix with lectin from *Galanthus nivalis* [snowdrop]) twice to procure complete purification from nucleosome and exosome bound circulating cfDNA. Remaining circulating cfDNA was extracted from the plasma purified from nucleosome and exosome as was described in Example 3. The total amount of residual DNA (recovered from patient plasma purified before from nucleosome- and exosome-bound circulating cfDNA) was about 50 μg. DNA was than resuspended in phosphate buffered saline (PBS) at pH 7.2 and used for an animal experiment as described below.

Eight 10 weeks old C57/BL6 male mice were intravenously injected with 1 μg of extracted cfDNA three times with 1 h interval. Animals were euthanized 4 hours following the last DNA injection for collecting blood.

Plasma creatinine levels were measured by an enzymatic assay. Plasma TNF-α, IFN-g, and IL-12 levels fluorescent magnetic bead-based immunoassay (Bio-Rad Laboratories, USA). Results are summarized in Table 3 below.

TABLE 3

| Parameter | Value prior first DNA injection | 4 h following last DNA injection. Mean ± SD |
|---|---|---|
| Creatinine | 0.063 ± 0.016 mg/dL | 0.,167 ± 0.020 mg/dL |
| IFN gamma | 18.9 ± 5.4 pg/ml | 46.1 ± 6.2 mg/ml |
| TNF alpha | 6.13 ± 2.5 pg/ml | 31.4 ± 5.4 pg/ml |
| IL12 | 17.1 ± 6.2 pg/ml | 278.4 ± 17.4 pg/ml |

Thus, cfDNA of plasma purified from nucleosome bound DNA and exosomes has strong proinflammatory activity and compromises organ function.

Example 11: Circulating cfDNA of Patient Plasma Purified from Nucleosome- and Exosome-Bound DNA but not Purified from Particle-Free DNA is Responsible for TLR9 Activation Activation of TLR9 receptors has been recently recognized as an important component in the development of systemic host-inflammatory response, organ failures, cancer invasion and metastasis, neuronal injury in stroke, autoimmunity, eclampsia and age dependent deregulation of immunity leading to age related proinflammatory status.

The patient was a 33 year old man with acute myeloid leukemia and an HLA-matched bone marrow transplant (BMT), followed by standard immunosuppression and antibiotic prophylaxis. About 1 month following BMT, the patient developed erythematous rash consistent with GVHD grade III and severe diarrhea. Plasma samples were taken at the patient's admission and purified subsequently with anti-histone H2A antibody and lectin affinity columns as described in the Example 2 (affinity matrix with anti-histone antibodies and affinity matrix with lectin from *Galanthus nivalis* (snowdrop)) or purified with histone H1.3 affinity column prepared as described in Example 1 (affinity matrix of cellulose beads coupled with histone H1.3).

HEK-Blue™ hTLR9 reporter cells (Invivogen) were rinsed with medium to detach them from the culture flask and cells were resuspended to the cell density specified by the manufacturer's protocol. 180 μl of cell suspension per well was stimulated for 24 h (37° C., 5% $CO_2$) with 60 μl of untreated patient plasma, patient plasma purified through both lectin and anti-histone antibody affinity columns or purified through an H1.3 affinity column (as a single step). After incubation, analysis of secreted embryonic alkaline phosphatase (SEAP) was performed using Quanti-Blue detection medium as described in the manufacturer's instructions. Detection of absorbance at 650 nm was measured using a microplate reader.

TABLE 4

| Plasma sample | OD (650 nm). Mean ± SD |
| --- | --- |
| Untreated sample | 0.82 + 0.11 |
| Sample, puified with lectin and anti-histone antibody affinity matrices/columns | 0.73 + 0.07 |
| Sample purified with, histone H1.3 affinity matrix/column | 0.21 + 0.05 |

Quantification of TLR9 activation was performed by reading the optical density (OD) at 620 nm. (N=3.) The results are shown in Table 4. Surprisingly, the elimination of exosomes- and nucleosome-bound circulating cfDNA prevented TLR9 activation by patient plasma to quite limited extent, while removal of substantially all types of particle-bound and unbound cfDNA, including dsDNA, ssDNA and oligonucleotides, prevented TLR9 activation by patient plasma almost completely.

Example 12: Preparation of Hyper-Branched Poly-L-Lysine Affinity Matrix (PLLAM) and Affinity Column Cationic poly-aminoacids like poly-L-lysine (PLL) are known to be efficient in condensing plasmid DNA into compact nanostructures and have been used for in vitro and in vivo binding of DNA.

Cationic DNA-binding polymer, namely hyper-branched poly-L-lysine (HBPL) was prepared as described in Kadlecova, Z. et al, A comparative study on the in vitro cytotoxicity of linear, dendritic and hyperbranched polylysine analogs, Biomacromolecules, v. 13 (2012) pp 3127-3137): 27.45 g of L-lysine monohydrochloride (reagent grade, ≥98%, Sigma-Aldrich, USA) was dissolved in 55 mL Milli-Q water and neutralized by (8.4 g KOH. Then, the solution was heated to 150° C. for 48 h under a stream of nitrogen. Then, to remove excess salt and remaining L-lysine, the polymerization product was dialyzed with dialysis membrane tubing against Milli-Q water (Snakeskin Dialysis Tubing, Thermo Fisher Scientific, Switzerland, molecular weight cut off: 3000 g/mol) The product of dialysis was freeze-dried and then fractionated with Sephadex G75 gel filtration column (GE Healthcare Life Science, Switzerland): the column was loaded with 50 mL of a 2 mg/mL HBPL solution in 0.01 M HCl and subsequently eluted with 0.01 M HCl. Fractions of 20 mL were collected and lyophilized. The fraction with 21000-32000 of weight-average molecular weight (as determined by size exclusion chromatography) was collected and lyophilized. Lyophilized fraction was dissolved in bidistilled water, dialysed against 0.1 M NaHCO$_3$ and used for further affinity matrix preparation. Agarose matrix which comprise immobilized HBPL was prepared by a conventional method as follows: cyanogen bromide-activated Sepharose 4B (wet weight 10 g, Sigma) was suspended in 10 ml of 0.1M NaHCO$_3$, mixed with 10 ml of 21000-32000 HBPL fraction (5 mg/ml in 0.1 M NaHCO$_3$), and stirred for 24 h at 4° C. The prepared HBPL Sepharose (4 mg of HBPL per ml bead suspension) was then poured in a polycarbonate column (1.0×12 cm) and washed with 750 ml of 0.1 M NaHCO$_3$, 750 ml of 0.5 M NaCl and adjusted to pH 9.2. The column was equilibrated with 0.05 M Tris-HCl buffer, pH 7.5. The prepared affinity column with hyper-branched poly-L-lysine affinity matrix (PLLAM) was stored at 4° C.

Example 13: Separation of Different Subtypes of Circulating cfDNA from the Blood of Patient with Neurodegenerative Disease Circulating cfDNA from patients with neurodegenerative disorders can pass through the blood brain barrier (BBB) and induce neuronal cell death. The use of deoxyribonuclease enzyme could abolish this effect. See Int. Pat. Appl. Pub. WO2016190780. To investigate the effect of different subtypes of circulating cfDNA on neuronal cell death and to see if purification of blood from all of nucleosome bound cfDNA, exosome bound cfDNA and unbound cfDNA including dsDNA, ssDNA and oligonucleotides might prevent neuronal cell death, the following experiments were performed.

For neuronal cultures, cerebral cortices were removed from embryonic day (E) 15-17 Sprague Dawley rat embryos. Cortical explants were dissected into pieces of about 200-400 μm$^2$ using fine needles and dissociated with the Papain Dissociation System (Worthington Biochemicals) according to the manufacturer's instructions and further kept on ice-cold minimum essential medium (Gibco). Neurons were plated on 13 mm diameter glass coverslips coated first with poly-D-lysine (10 μg/mL in PBS) followed by laminin (10 μg/mL in PBS) (Gibco) and cultured for 24 hrs. at 37° C. in a humidified 8% CO$_2$ (v/v) atmosphere for 24-48 hrs. in neurobasal medium with 1% (v/v) Antibiotic-Antimycotic (Gibco).

After an initial period of culturing the cell culture media was diluted twice (v/v) with one of the following plasma samples with further culturing for another 24 hrs: (a) plasma of a healthy 20 year old donor, (b) plasma of the patient with rapidly progressed Alzheimer's disease (AD), (c) plasma of the same AD patient treated for 6 hours with 5 μg/mL of DNase I (Pulmozyme, Genentech), (d) plasma of the same AD patient following passage through both of lectin and anti-histone H2A antibody affinity columns (prepared as described in Example 2, i.e. affinity matrix with anti-histone H2A antibodies and affinity matrix with lectin from *Galanthus nivalis* [snowdrop]), and (e) plasma of the same AD patient following passage through histone H1.3 affinity column (the matrix was prepared as described in Example 1, i.e. affinity matrix of cellulose beads coupled with histone H1.3) and placed to 0.8×9 cm polycarbonate column (up to 80% of column volume), with the volume of plasma samples passed through the corresponding columns being about 2.0 mL.

Figure 5:
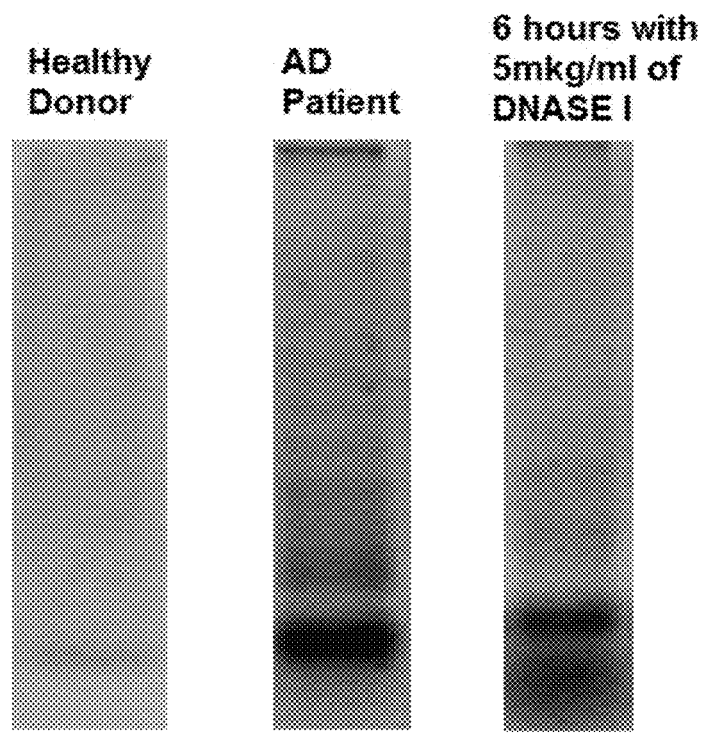
FIG. 5 shows an electrophoretic profile of circulating cfDNA used in cell culture experiments.
Figure 5:
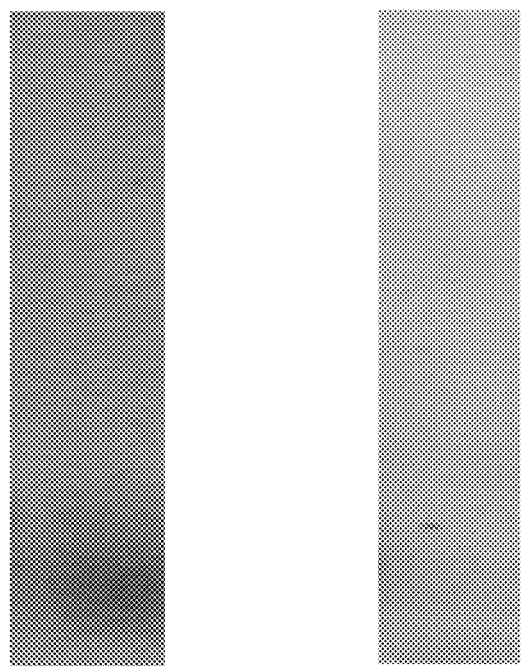

The electrophoretic profile of circulating cfDNA from plasma samples used in cell culture experiments are presented in FIG. 5.

Only a limited amount of nucleosome-bound circulating cfDNA in the form of mononucleosomes was detected in the plasma of a healthy donor. High levels of nucleosome bound circulating cfDNA in the form of mono and oligonucleosomes were detected in the plasma of an AD patient. Treatment of AD patient plasma with DNase I enzyme resulted in a decrease of DNA content in oligonucleosomal and mononucleosomal fractions, but with a significant increase of DNA in subnucleosomal fraction (~below 147 base pairs in length). Plasma of an AD patient purified with lectin and anti-histone H2A antibody affinity columns did not contain nucleosome-bound circulating cfDNA but only subnucleosomal (i.e., unbound) cfDNA. Plasma of an AD patient treated with histone H1.3 affinity column (as a single step) did not contain circulating cfDNA.

Induction of apoptic cell death marker Caspase 3 was determined in dissociated cortical neurons cultured following 24 hours of exposure to plasma samples. Cells were fixed in 4% (w/v) paraformaldehyde (PFA) and incubated for 1 hour with cleaved Caspase 3 antibody (Abcam) diluted 1:500 in PBS. Cells were washed and incubated for 1 hour with goat anti-rabbit polyclonal Alexa Fluor 488 antibodies (Invitrogen) in PBS prior to washing and counting.

TABLE 5

| Plasma sample | % of cells positive for Caspase 3; median for three repetitive cell cultures |
|---|---|
| Healthy 20 Y donor sample, untreated | 5.3% |
| AD patient sample, untreated | 30.0% |
| AD patient sample treated with DNase I | 15.7% |
| AD patient sample purified with lectin and anti-histone antibody affinity matrices/columns | 17.7% |
| AD patient sample purified with H1 affinity matrix/column | 7.7% |

The results are shown in Table 5. Thus, purification of blood from substantially all types of cfDNA, including nucleosome-bound cfDNA, exosome-bound cfDNA and unbound cfDNA (including dsDNA, ssDNA and oligonucleotides) prevents neuronal cell death to substantially higher extent than a simple purification from nucleosome-bound cfDNA and exosome-bound cfDNA and even better than cleavage of circulating cfDNA in plasma with DNase I enzyme, probably due to release of byproducts of DNA enzymatic degradation or low sensitivity of circulating cfDNA to DNase I.

Example 14: Reactivation of Endogenous Deoxyribonuclease

Deoxyribonuclease enzyme (DNase) is the principal enzyme responsible for degradation of high molecular weight DNA in circulation. Multiple studies show that deoxyribonuclease activity is suppressed in certain conditions involving raise of circulating cfDNA in blood, such as cancer, metastatic cancer, autoimmune disease, sepsis, infertility, (Tamkovich S N, Circulating DNA and DNase activity in human blood. Ann N Y Acad Sci. 2006 September; 1075:191-6; Martinez-Valle, DNase 1 activity in patients with systemic lupus erythematosus: relationship with epidemiological, clinical, immunological and therapeutical features. Lupus. 2009 April; 18(5): 418-23; EP20070827224; Travis J Gould, Cellular and Biochemical Properties of Cell-Free DNA: A Prognostic Marker In Severe Sepsis Patients, Blood 2011,118:2169)

To assess how reduction of nucleosome-bound cfDNA, exosome-bound cfDNA and unbound cfDNA including dsDNA, ssDNA and oligonucleotides affects DNaseI activity in plasma the following experiment was performed. cfDNA was measured in plasma using method described by Goldstein (Goldshtein, H. et al., A rapid direct fluorescent assay for cell-free DNA quantification in biological fluids, Annals of Clinical Biochemistry, Vol 46, Issue 6, pp. 488-494). SYBR® Gold Nucleic Acid Gel Stain, (Invitrogen) was diluted first at 1:1000 in dimethyl sulphoxide and then at 1:8 in phosphate-buffered saline. 10 µL of plasma samples were applied 96-well plates. 40 µl of diluted SYBR Gold was added to each well (final dilution 1:10,000) and fluorescence was measured with a 96 well fluorometer at an emission wavelength of 535 nm and an excitation wavelength of 485 nm.

DNase I western blotting was performed in plasma samples separated using 10% SDS-PAGE gels, transferred onto polyvinylidene difluoride (PVDF) blotting membranes, and incubated with goat anti-human DNase I antibodies (Santa Cruz Biotechnology). Binding was visualized using SuperSignal Chemiluminescent Substrate (Pierce) after incubation with HRP-conjugated anti-goat IgG.

Serum deoxyribonuclease activity was measured using ORG590 (Orgentec) according to the manufacturer's protocol Detection was performed using microplate photometer (Multiscan FC) at 450 nm with a correction wavelength of 620 nm.

Figure 6:
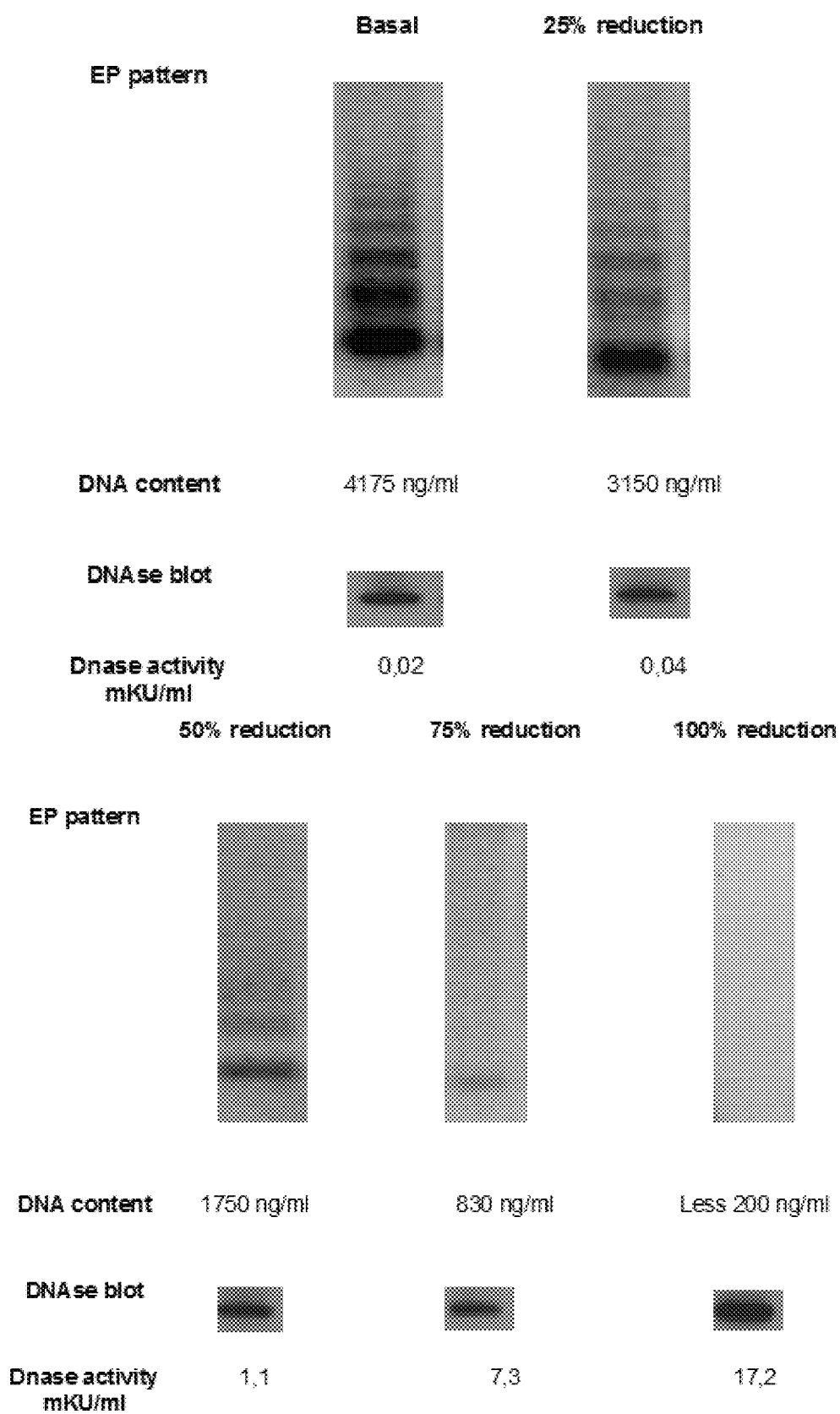
FIG. 6 shows an electrophoretic profile of circulating cfDNA, DNase I western blot and quantification of DNase I activity and circulating cfDNA.

Blood was sampled from 56-year-old female patient with breast cancer, multiple metastasis in lungs, liver and mediastenum (T4N3M1). 5 mL plasma aliquote was subjected to multiple runs through 1 mL polycarbonate column (0.5×5 cm) containing 0.5 mL of histone H1.3 affinity matrix: assessment of electrophoretic profile of circulating cfDNA, DNAse western blot and quantification of deoxyribonuclease activity and circulating extracellular content were measured after each column run. The results are summarized in FIG. 6.

The electrophoretic assessment of circulating cfDNA profile showed a continuous decrease of all fractions content alongside with increasing number of column runs. That observation was confirmed by direct quantification of circulating cfDNA in plasma. A comparable amount of DNase I enzyme as detected by western blot was present in patient plasma initially. However enzymatic activity of DNase I was heavily suppressed and became meaningful only after 4 column runs when the amount of circulating cfDNA was decreased approximately twice.

Thus the apheresis according current invention wherein the overall circulating levels of cfDNA in said mammal is reduced by at least 50% might reactivate the activity of endogenous DNase I enzyme, which is beneficial for patients who require lowering of circulating cfDNA levels.

Based on highest reported levels of circulating cfDNA of approximately 5000 ng/mL (which are reported for some advanced cancer, septic patients and patient with trauma) the affinity column or combination of affinity columns with binding capacity of 30 mg would be able to provide almost complete purification of patient plasma from all of nucleosome bound cfDNA, exosome bound cfDNA and unbound cfDNA including dsDNA, ssDNA and oligonucleotides Example 15: Preparation of an Affinity Column that Contains Antinucleosome Antibody Affinity Matrix (ANAM)

A mouse monoclonal nucleosome-specific antibody was prepared using MRL/Mp (−)+/+ mouse according to the method described in M. J. Losman Monoclonal autoantibodies to subnucleosomes from a MRL/Mp (−)+/+ mouse. Oligoclonality of the antibody response and recognition of a determinant composed of histones H2A, H2B, and DNA. J Immunol Mar. 1, 1992, 148 (5) 1561-1569). Prepared monoclonal (IgG) antibodies (mAbs), named here as AN-1 and AN-44, correspondingly, were selected on the basis of their ability for selective binding of nucleosomes but not components of nucleosomes like core histones or DNA. (Kees Kramers, Specificity of monoclonal anti-nucleosome autoantibodies derived from lupus mice, Journal of Autoimmunity, V. 9, Issue 6, 1996, P. 723-729). The relative affinity of AN-1 and AN-44 to nucleosomes and histone and non histone components of nucleosome are summarized in Table 6 below.

TABLE 6

| MAbs | AN-1 | AN-44 |
|---|---|---|
| Nucleosome | 17,400 | 12,000 |
| DNA | 200 | 300 |
| Histones H2A/H2B | <10 | <10 |
| Histones H3/H4 | <10 | <10 |

1 mL HiTrap NHS activated HP column prepacked with NHS activated Sepharose High Performance (GE Healthcare) was used for affinity matrix/cartridge preparation. 200 µg of AN-1 were coupled according to the manufacturer's procedure to NHS activated Sepharose Based on the affinities data presented at the table above it is obvious that ANAM binds only nucleosome-bound circulating cfDNA but not unbound cfDNA, including dsDNA, ssDNA and oligonucleotides.

Thus, in order to secure binding of unbound cfDNA, including dsDNA, ssDNA and oligonucleotides, in animal experiment two sequential columns were used. One column with anti-nucleosome antibody affinity matrix (ANAM) was prepared as described above in this example. A second column with polyamidoamine dendrimer affinity matrix was prepared as described in Example 4.

Example 16: Apheresis Procedure

Chronic venous catheters were inserted into the femoral vein and the vena jugulars of experimental rats under general anesthesia (i.p. injection of 0.8 mg xylazine and 4 mg ketamine). Catheters were flushed three times per week with heparinized saline during the study. Before each apheresis procedure, a heparin bolus was given (90 IU/100 g body weight (b.w.). The extracorporeal system was fully filled with heparinized saline and thereafter, the catheter endings were connected with the extracorporeal system.

For animal apheresis experiments, the affinity columns described in this specification were fitted with inlets and outlets for further embedding these prepared affinity columns to second (plasma) circuit of extracorporeal/apheresis system.

In the first circuit of the system, blood was pumped (Rotary peristaltic Mini-pump, Fisher Scientific) from the animal (femoral vein) via a plasma separator (Saxonia medical, Radeberg, Germany) and returned to the animal by a venous catheter inserted to jugular vein. The separated plasma entered the second circuit (supported by second Rotary peristaltic Mini-pump) and passed through affinity cartridges (according to the specific examples of the apheresis procedures described in this specification), and returned to animal body via polymer line also connected to the catheter inserted into jugular vein.

Example 17: Apheresis Treatment of Sepsis and Septic Kidney Injury

Classic induced sepsis model by the method of cecal ligation and puncture (CLP) were established. Female Sprague-Dawley (SD) rats of 350-400 g body weight were used. Animals were anesthetized with sodium pentobarbital (50 mg/kg intraperitoneally).

A midline abdominal incision about 1.5 cm was performed. The cecum mesentery was dissected to expose the cecum. Then, the cecum was ligated between the terminal and ileocecal valve so that intestinal continuity was maintained. Then, the cecum was perforated by single through-and-through puncture with a 21-gauge needle in the central segment of ligation. The tied segment was gently pressed to ensure that a small amount of feces was extruded on to the surface of the bowel. The cecum was returned to the abdominal cavity. The surgical wound was sutured layer by layer with absorbable suture for the muscle layer and with surgical staples for the skin. After operation, the rats were injected with 10 ml/kg warm 0.9% sodium chloride for injection and after recovery the animals were randomly divided into three groups (Groups 1-3; 6 animals in each group) according to the treatment.

The apheresis treatment was performed as was described in Example 16. The apheresis procedure was carried out twice: on day 1 (24 hrs. after CLP), and day 3 (72 hrs. after CLP). 6 rats get apheresis procedure using column/cartridge with antinucleosome antibody affinity matrix (ANAM) prepared as specified in Example 15, and 6 rats get apheresis procedure using column/cartridge containing PAMAM dendrimer affinity matrix (PDAM) prepared as specified in Example 4. Six rats (negative control group) get apheresis procedure with cartridge that was loaded with corresponding volume of unmodified support cartridge). Level of acute kidney injury (renal function) was assessed by measurement of serum creatinine and blood urea nitrogen (BUN) levels with Roche Reflotron Plus (Roche Diagnostics before each apheresis procedure. Circulating cfDNA was extracted from 100 µL plasma samples with conventional THP (Triton-Heat-Phenol) method (Breitbach et al., PLoS ONE, 2014, 9(3):e87838). DNA was quantified with the PicoGreen assay (Molecular Probes, Netherlands) following the manufacturer's instructions and cfDNA changes were expressed as percentage of DNA level to baseline i.e. to the level before first apheresis procedure. For negative control group the columns/cartridges containing corresponding amount of unmodified support (Macroporous Bead Cellulose MT 500, particle size 100-250 µm, Iontosorb, Czech Republic, washed twice with 98% ethanol and bidistilled water) were prepared. The survival rate (120 hours after CLP) was assumed as main parameter of treatment efficacy of sepsis. The allocation of the animals and the results are shown in Table 7, below.

TABLE 7

| Hours post CLP | 24 | 48 | 72 | 96 | 120 |
|---|---|---|---|---|---|
| CLP + apheresis with unmodified support cartridge (Negative Control); n = 6 | | | | | |
| Circulating levels of cfDNA (before/after apheresis) | 100%/100% | | 137%/137% | | |

TABLE 7-continued

| Hours post CLP | 24 | 48 | 72 | 96 | 120 |
|---|---|---|---|---|---|
| Serum creatinine, µmol/L | 140 ± 20 | 160 ± 12 | 194 ± 31 | 215 ± 16 | |
| Blood urea nitrogen (BUN), mmol/L | 11.2 ± 2.1 | 14.9 ± 2.8 | 16.8 ± 3.5 | 18.2 ± 3.0 | |
| Survival | | | | | 1 of 6 |
| CLP + apheresis with ANAM cartridge; n = 6 | | | | | |
| Circulating levels of cfDNA (before/after apheresis) | 100%/58% | | 66%/32% | | |
| Serum creatinine, µmol/L | 136 ± 12 | 139 ± 13 | 145 ± 14 | 140 ± 13 | |
| Blood urea nitrogen (BUN), mmol/L | 12.3 ± 2.2 | 12.8 ± 2.2 | 13.5 ± 2.5 | 14.7 ± 2.1 | |
| Survival | | | | | 3 of 6 |
| CLP + apheresis with PDAM cartridge, n = 6 | | | | | |
| Circulating levels of cfDNA (before/after apheresis) | 100%/21% | | 33%/12% | | |
| Serum creatinine, µmol/L | 138 ± 12 | 100 ± 13 | 105 ± 14 | 111 ± 16 | |
| Blood urea nitrogen (BUN), mmol/L | 12.4 ± 1.7 | 8.4 ± 1.0 | 10.4 ± 2.2 | 12.6 ± 3.7 | |

The results show that the PDAM apheresis device was able to capture substantially all types of cfDNA, including nucleosome-bound cfDNA, exosome-bound cfDNA and unbound cfDNA (including dsDNA, ssDNA and oligonucleotides) and provided a better therapeutic efficacy and more efficiently reduced the level of circulating cfDNA in sepsis and septic kidney injury.

Example 18: A Apheresis Treatment of Chemotherapy Related Toxicity Sins 18 female Sprague-Dawley (SD) rats of 300-350 g body weight were prepared for apheresis procedure as described in Example 16 and received single intravenous bolus injection of paclitaxel (Taxol, Bristol-Myers Squibb S.r.L.) at 10 mg/kg dose. The apheresis procedure was started 4 hours following paclitaxel injection and continued for 12 hours; 6 rats get apheresis procedure using column/cartridge with antinucleosome antibody affinity matrix (ANAM), and 6 rats get apheresis procedure using column/cartridge containing hyper-branched poly-L-lysine affinity matrix (PLLAM). 6rats(negativecontrol) get apheresis procedure with cartridge that was loaded with corresponding volume of unmodified support (Sepharose 4B).

Circulating cfDNA levels were quantified and presented as described in Example 17 (with cfDNA expressed as percentage of DNA level to baseline). The survival rate (24 hours after bolus) was assumed as main parameter of treatment efficacy. The allocation of the animals and the results are shown in Table 8 below.

TABLE 8

| Hours post Paclitaxel bolus | 4 h | 16 h | 24 h |
|---|---|---|---|
| Paclitaxel + apheresis with unmodified support cartridge (Negative Control) n = 6 | | | |
| Circulating levels of cfDNA (before/after apheresis) | 100% | 230% | |
| Survival | | | zero from 6 |
| Paclitaxel + apheresis with ANAM cartridge; n = 6 | | | |
| Circulating levels of cfDNA (before/after apheresis) | 100% | 165% | |
| Survival | | | 2 from 6 |
| Paclitaxel + apheresis with sequential PLLAM cartridge, n = 6 | | | |
| Circulating levels of cfDNA (before/after apheresis) | 100% | 65% | |
| Survival | | | 5 from 6 |

The results show that PLLAM apheresis device was able to capture substantially all types of cfDNA, including nucleosome-bound cfDNA, exosome-bound cfDNA and unbound cfDNA (including dsDNA, ssDNA and oligonucleotides) provide better protection/therapeutic efficacy and more efficiently reduced the level of circulating cfDNA in animals poisoned by a chemotherapeutic drug.

Example 19. Purification/Apheresis of Plasma cfDNA with One Cartridge that Captures Nucleosome- and Exosome-Bound DNA and Another Cartridge that Captures Unbound cfDNA Including dsDNA, ssDNA and Oligonucleotides For the measurements of plasma cfDNA level, cfDNA was extracted from 500 µL plasma samples using modified HTP method (Xue, X., et al. Optimizing the yield and utility of circulating cell-free DNA from plasma and serum, Clinica Chimica Acta, V.404 (2009), pp. 100-104) and quantified using the PicoGreen assay (Molecular Probes, Netherlands) according to the manufacturer's instructions.

When cfDNA was undetectable in a sample by PicoGreen assay, the absence of cfDNA in the samples was further confirmed by DNA electrophoresis in agarose gel in a manner described in the specification above.

For apheresis/purification procedures plasma samples were gradually applied to the corresponding affinity columns and allowed to flow through.

A 2.0 mL plasma sample obtained from 67-year-old septic shock patient was purified consequently through an ANAM affinity column. The ANAM affinity column (which captures nucleosome-bound cfDNA) was prepared on the basis of 1 mL HiTrap NHS activated HP column (as described in Example 15) and lectin affinity column (which captures exosome-bound cfDNA) was prepared as described in the Example 2 (affinity matrix with lectin from *Galanthus nivalis* [snowdrop]).

Figure 7:
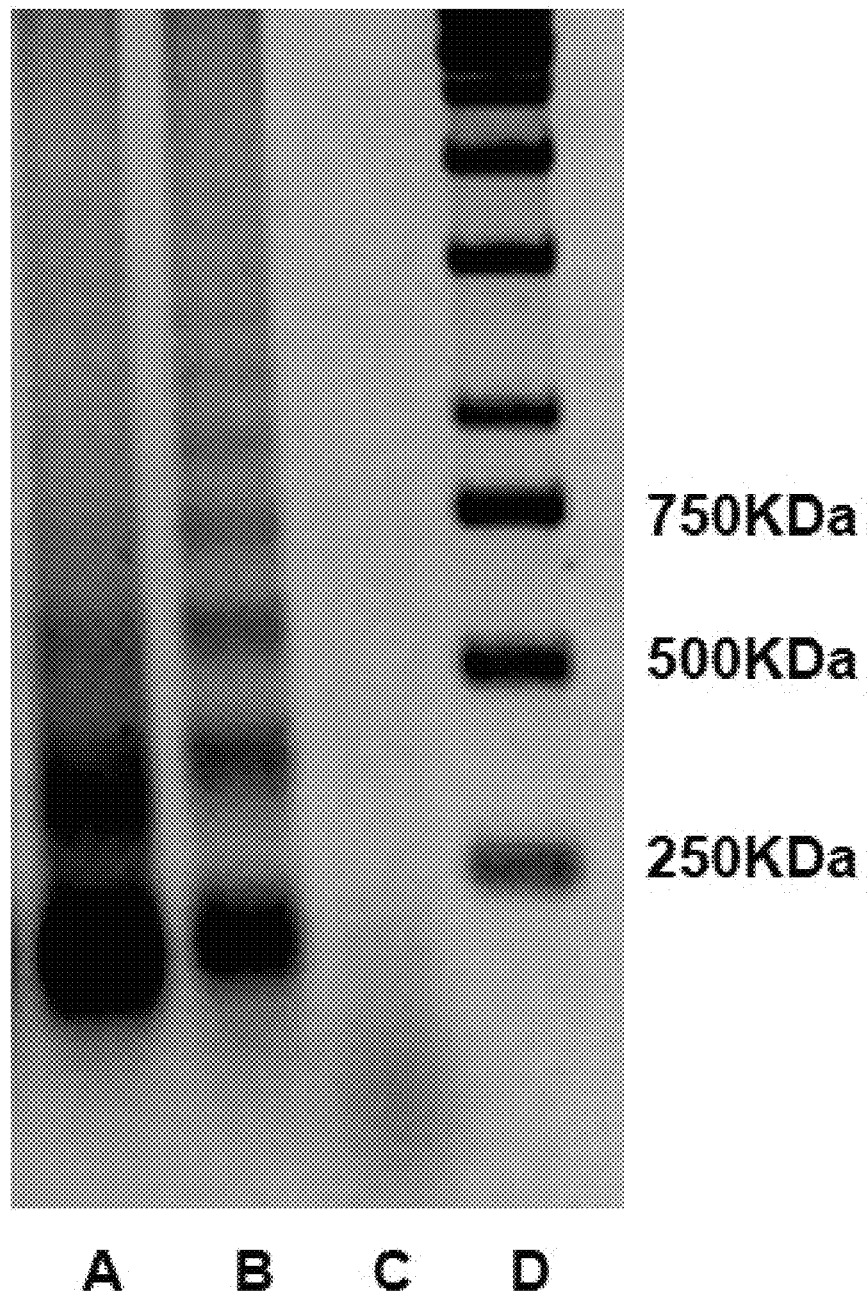
FIG. 7 shows an electrophoretic profile of circulating cfDNA from plasma of a patient with sepsis.

Initial cfDNA level in patient plasma was 1150 ng/mL with significant presence of substantially all types of cfDNA visualized by DNA electrophoresis in agarose gel (See FIG. 7, lane A). The level of cfDNA in plasma following first run through combination of ANAM and lectin affinity columns has decreased to 350 ng/mL. Partially purified patient plasma was further subjected to second run through same combination of fresh ANAM and lectin affinity columns. The level of cfDNA in plasma following second run remained unchanged with visible amounts of cfDNA of non-nucleosomal origin with molecular weight of up to 750 kDa visualized by DNA electrophoresis in agarose gel with fluorescent DNA dye staining (See FIG. 7, lane C).

The experiment made clear that inability of ANAM and lectin affinity columns to completely purify patient plasma from cfDNA did not relate to overall binding capacity of the AMAM and lectin affinity columns combination but rather to its inability to capture cfDNA of non-nucleosomal or non-exosomal origin from patient plasma. In order to confirm this we further purified the sample through anti-DNA antibody affinity column prepared as described in Example 7 (matrix of agarose coupled with high affinity mouse monoclonal IgM Anti-ds+ss DNA).

Following one purification run the level of cfDNA in patient plasma became undetectable as measured by PicoGreen assay. This observation was further confirmed by absence of visible DNA material following DNA electrophoresis in agarose gel.

Thus, use of two sequential affinity columns/cartridges, wherein one column/cartridge captures nucleosome-bound DNA and exosome-bound DNA and another column/cartridge captures unbound cfDNA including dsDNA, ssDNA and oligonucleotides, is very effective for purification/apheresis of patient blood from all type of circulating cfDNA.

Another 2 mL plasma sample from the same patient were purified consequently through DNA-intercalator affinity column (prepared as described in Example 8, i.e., cellulose beads coupled with Hoechst 33342) and anti-DNA antibody affinity column (prepared as described in Example 7, i.e., matrix of agarose coupled with high affinity mouse monoclonal IgM anti-DNA). The level of cfDNA in plasma following first run through combination of DNA-intercalator and anti-DNA antibody affinity columns has decreased to 475 ng/mL with cfDNA of different origin visualized by DNA electrophoresis in agarose gel (FIG. 7, Lane B). This partially purified patient plasma was further subjected to a second run through the same combination of fresh DNA-intercalator and anti-DNA antibody affinity columns. The level of cfDNA in plasma following the second run in the patient plasma became undetectable as measured by PicoGreen assay. This observation was further confirmed by absence of visible DNA material following DNA electrophoresis in agarose gel with fluorescent DNA dye staining.

Thus, the use of a combination of columns/cartridges containing matrices which bind substantially all types of cfDNA (including nucleosome-bound cfDNA, exosome-bound cfDNA and unbound cfDNA [including dsDNA, ssDNA and oligonucleotides]) according to the invention permits capture of an unusually high amount of cfDNA.

Example 20. Purification/Apheresis of Plasma from the Portal Vein to Purify Blood of Rats with Acute Pancreatitis Six male Sprague-Dawley rats, 250-350 grams were used in the experiment. All surgical procedures were performed on a heated operating table under general anaesthesia with i.p. injection of 0.8 mg xylazine and 4 mg ketamine.

Acute pancreatitis was induced as follows. During laparotomy the papilla of Vater was cannulated transduodenally using a 24G Abbocath®-T i.v. infusion cannula. Before pressure monitored infusion of 0.5 mL sterilized glycodeoxycholic acid in glycylglycine-NaOH-buffered solution (10 mmol/L, pH 8.0, 37° C.), the common bile duct was clamped and bile and pancreatic fluid were allowed to drain through the cannula. Directly after infusion, hepato-duodenal bile flow was restored by removal of the clamp. The puncture hole in the duodenum was carefully closed using an 8.0 polyprolene serosal suture.

After closure of the abdomen in Rats 1, 2 and 3, chronic venous catheters were inserted into the femoral vein and the jugular vein as described in Example 16.

Rats 4, 5 and 6 had a portal vein catheter implanted into the hepatic portal vein caudal of the liver as described by Strubbe (Strubbe J. H. et al, Hepatic-portal and cardiac infusion of CCK-8 and glucagon induce different effects on feeding. Physiol Behav 46: 643-646, 1989).

The apheresis treatment was performed as described in Example 16 using PDAM affinity cartridge, prepared as was described in Example 4 and fitted with polypropylene inlet and outlet. The apheresis procedure was carried out daily during days 1-3 with 12 hours duration of each apheresis procedure.

The survival rate (96 hours following induction of pancreatitis) was assumed as a main parameter of treatment efficacy. For quantification of cfDNA of rat and cfDNA of bacteria origin (i.e., bacterial load), total cfDNA was isolated from 200 µL rat plasma samples using a QIAamp DNA Mini Kit according to the manufacturer's instructions. cfDNA concentration on the plasma samples were measured by quantitative polymerase chain reaction (PCR) using the ABI PRISM 7700 Sequence Detector (Applied Biosystems) and TaqMan Universal PCR Master Mix (Applied Biosystems) according to the manufacturer's protocol. For quantification of cfDNA of bacterial origin, specific primers and a probe were designed for the conserved regions of bacterial 16S rDNA: the forward primer, (SEQ ID NO: 1)
5'-TCCTACGGGAGGCAGCAGT-3', the reverse primer (SEQ ID NO: 2)
5'-GGACTACCAGGGTATCTAATCCTGTT-3' and the probe (SEQ ID NO: 3)
(6-FAM)-5'-CGTATTACCGCGGCTGCTGGCAC-3'-(TAMRA)

(see: Mangala, A.; Nadkarni, A. Determination of bacterial load by real-time PCR using a broad-range (universal) probe and primers set. Microbiology, 2002, vol. 148, pp. 257-266). TaqMan Gene Expression Assay rat β-actin Rn00667869_m1 (Applied Biosystems) was used for amplification of rat genomic cfDNA Survival/outcome and the results of each PCR (Ct, i.e. threshold cycle value) for rat β actin gene and bacterial 16S rDNA in blood plasma sampled from jugular vein are presented in Table 9.

TABLE 9

| | Vein from which the blood was diverted. | β actin gene Ct* | 16S rDNA Ct* | Survival/ Outcome |
|---|---|---|---|---|
| Rat 1 | Femoral vein | 29.49 ± 0.161 | 24.22 ± 0.096 | Alive at 96 h |
| Rat 2 | Femoral vein | 29.2 ± 0.379 | 23.85 ± 0.218 | Dead at 82 h |
| Rat 3 | Femoral vein | 28.62 ± 0.278 | 23.59 ± 0.109 | Alive at 96 h |
| Rat 4 | Portal vein | 30.26 ± 0.176 | 27.89 ± 0.112 | Alive at 96 h |
| Rat 5 | Portal vein | 30.26 ± 0.21 | 25.78 ± 0.155 | Alive at 96 h |
| Rat 6 | Portal vein | 30.44 ± 0.151 | 29.42 ± 0.341 | Alive at 96 h |

*Mean ± SD of three independent runs. Ct values are natural logarithmic and inverse to the amount of nucleic acid or gene of interest in the sample. The Ct is the cycle number at which the fluorescence generated within a reaction crosses the threshold line.

The results show that diverting/removing the blood for apheresis into an apheresis device according to the invention from portal vein resulted in better (as compared to diverting of the blood from femoral, i.e., non-regional vein) survival and more effective purification of blood from cfDNA (including cfDNA of bacterial origin) in rats with acute pancreatitis.

Thus, in clinical circumstances where the pathological process responsible for the release of cfDNA (tumor growth, septic or aseptic inflammation, bacterial DNA release) originates from areas/regions drained primarily by portal vein (esophagus, gastric, intestinal, splenic, pancreatic, gallbladder, peritoneal cavity) diverting the blood for apheresis procedure from the portal vein might be beneficial.

Example 21. Comparison of cfDNA Removal from Patient Plasma by Histone H1 Affinity Matrix, PAMAM Dendrimer Affinity Matrix and Poly-L-Lysine Affinity Matrix (PLLAM)

Poly-L-lysine affinity matrix (PLLAM) was produced as specified in Example 12. PAMAM dendrimer affinity matrix (PDAM) was produced as specified in Example 4. Histone H1 affinity matrix was produced as specified in Example 1.

Model plasma enriched with cfDNA was produced by mixing of plasma of healthy volunteer with marker DNA (1 kbp plus DNA Ladder, Invitrogen) to the final cfDNA concentration of 10 μg/ml. Adsorption capacity of poly-L-lysine affinity matrix (PLLAM), PAMAM dendrimer affinity matrix (PDAM) and histone H1 affinity matrix with respect to model plasma enriched with artificial 1 kbp plus DNA Ladder was tested by volume adsorption method with affinity matrix: plasma ratio 1:5 (100 μl of affinity matrix was mixed with 500 μl of model plasma) for 1 hour at 37° C. under slow rotation. Ethanolamine Sepharose FF was used as a control. Plasma samples were analyzed by 1% agarose gel electrophoresis using E-Gel Invitrogen system prior to incubation and upon sedimentation of affinity matrix. cfDNA was extracted from patient plasma using QIAamp DNA Blood Mini Kit, Quagen and quantified with Qubit 3.0 fluorimeter. Same affinity matrixes were incubated with plasma of the patient diagnosed with odontogenic-related sepsis with affinity matrix: plasma ratio 1:10 (100 μl of affinity matrix was mixed with 1 ml of patient plasma) using the same incubation conditions. In one hour, affinity matrix was removed by centrifugation. Plasma samples were analyzed by 1% agarose gel electrophoresis using E-Gel Invitrogen system prior to incubation and upon sedimentation of affinity matrix. Ethanolamine Sepharose FF was used as a control. cfDNA was extracted from patient plasma using QIAamp DNA Blood Mini Kit, Quagen and quantified with Qubit 3.0 fluorimeter. cfDNA quantification data are presented in Table 10, below.

TABLE 10

| | cfDNA content in model plasma; ng/ml, median ± SD | | | | |
|---|---|---|---|---|---|
| | Prior to incubation | After incubation | | | |
| | | Control | H1.3 | PDAM | PLLAM |
| Model plasma enriched with cfDNA | 992 ± 24 | 942 ± 17 | 44 ± 19 | 92 ± 23 | 83 ± 24 |
| Plasma from patient with odontogenic-related sepsis | 1832 ± 43 | 1648 ± 17 | 57 ± 17 | 488 ± 24 | 392 ± 43 |

Figure 8:
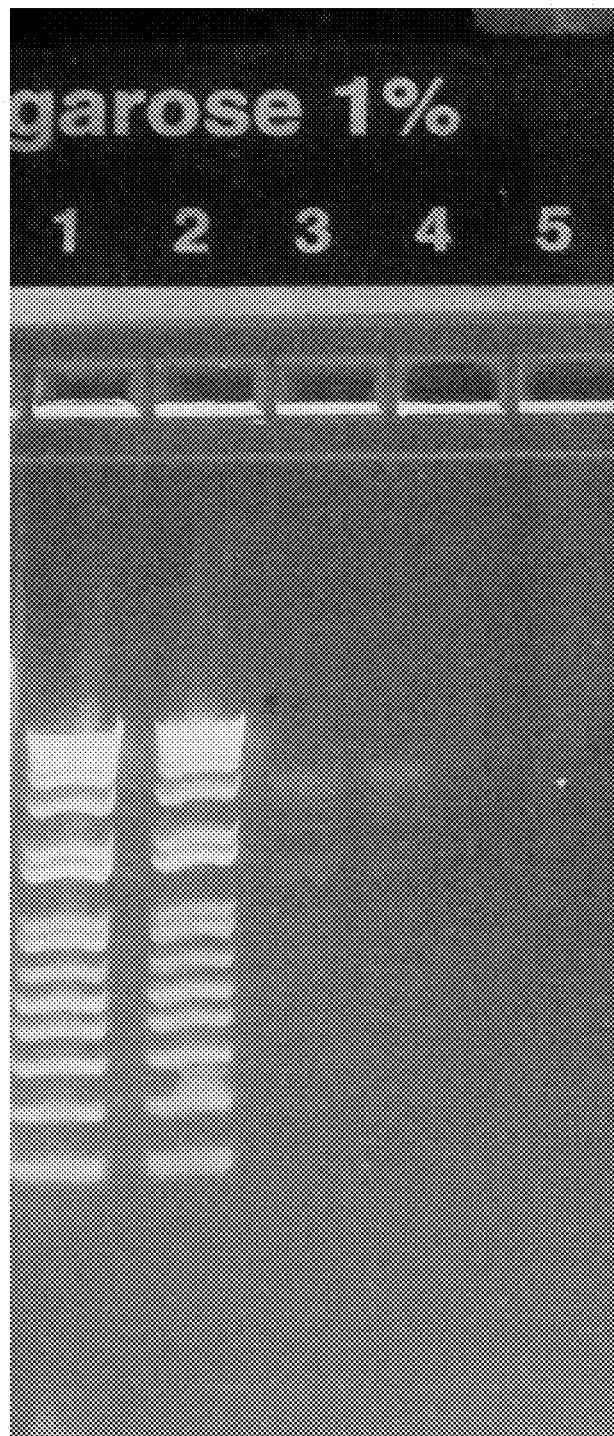
FIG. 8 shows the results of 1% agarose gel electrophoresis of model plasma enriched with cfDNA prior and following the volume adsorption test. Lane 1 is model plasma enriched with cfDNA prior to incubation; lane 2 is model plasma enriched with cfDNA following incubation with ethanolamine Sepharose FF control; lane 3 is model plasma enriched with cfDNA following incubation with PDAM; lane 4 is model plasma enriched with cfDNA following incubation with PLLAM; lane 5 is model plasma enriched with cfDNA following incubation with H1.3 affinity matrix.
Figure 9:
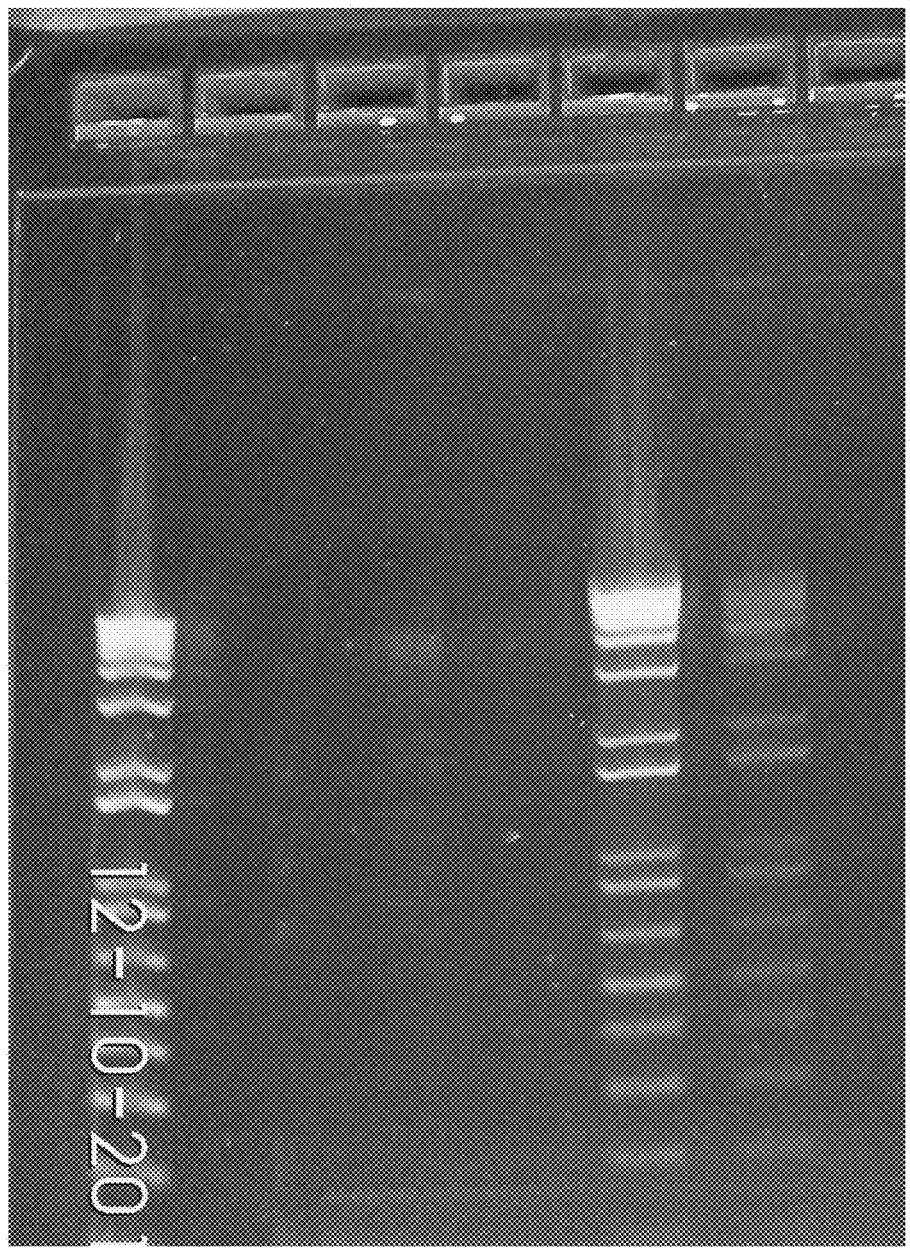
FIG. 9 shows the results of 1% agarose gel electrophoresis of plasma of the patient diagnosed with odontogenic-related sepsis prior to and following the volume adsorption test. Lane 1 is plasma of the patient with odontogenic-related sepsis following incubation with ethanolamine Sepharose FF control; lane 2 is distilled water blank line; lane 3 is plasma of the patient with odontogenic-related sepsis following incubation with H1.3 affinity matrix; lane 4 is distilled water blank line; lane 5 is plasma of the patient with odontogenic-related sepsis following incubation with PDAM; lane 6 is plasma of the patient with odontogenic-related sepsis following incubation with PLLAM.

It appears that poly-L-lysine affinity matrix (PLLAM), PAMAM dendrimer affinity matrix (PDAM) and histone H1 affinity matrix have equal capacity to remove model cfDNA from model plasma enriched with cfDNA, but histone H1 affinity matrix is significantly superior in removing cfDNA from patient plasma. The finding was confirmed by electrophoretic analysis of the samples (see FIGS. 8 and 9).

Volume adsorption test in model plasma with of poly-L-lysine affinity matrix (PLLAM), PAMAM dendrimer affinity matrix (PDAM) and histone H1 affinity matrix yielded almost same electrophoretic picture with marginal cfDNA content.

Volume adsorption test in model plasma with poly-L-lysine affinity matrix (PLLAM), PAMAM dendrimer affinity matrix (PDAM) and histone H1 affinity matrix yielded different electrophoretic picture with marginal cfDNA content following incubation with histone H1 affinity matrix but meaningful cfDNA content following incubation with poly-L-lysine affinity matrix and PAMAM dendrimer affinity matrix.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A device comprising one or more affinity matrices, wherein said one or more affinity matrices are capable of capturing nucleosome-bound cell free DNA (cfDNA), exosome-bound cfDNA, and unbound cfDNA from a bodily fluid of a subject, wherein at least one of said one or more affinity matrices comprises a linker histone.

2. The device of claim 1, wherein the unbound cfDNA comprises dsDNA, ssDNA and oligonucleotides.

3. The device of claim 1, wherein linker histone is human H1.3 linker histone.

* * * * *